US011102424B2

(12) United States Patent
Ueda

(10) Patent No.: US 11,102,424 B2
(45) Date of Patent: Aug. 24, 2021

(54) MEDICAL OBSERVATION APPARATUS AND MEDICAL OBSERVATION SYSTEM

(71) Applicant: Sony Olympus Medical Solutions Inc., Tokyo (JP)

(72) Inventor: Masaaki Ueda, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 87 days.

(21) Appl. No.: 16/537,641

(22) Filed: Aug. 12, 2019

(65) Prior Publication Data
US 2020/0068142 A1 Feb. 27, 2020

(30) Foreign Application Priority Data

Aug. 21, 2018 (JP) .............................. JP2018-154664

(51) Int. Cl.
| | |
|---|---|
| *H04N 5/262* | (2006.01) |
| *G06F 3/14* | (2006.01) |
| *H04N 5/225* | (2006.01) |
| *H04N 13/239* | (2018.01) |
| *H04N 13/25* | (2018.01) |
| *H04N 5/232* | (2006.01) |
| *A61B 90/00* | (2016.01) |

(52) U.S. Cl.
CPC ......... *H04N 5/2628* (2013.01); *A61B 90/361* (2016.02); *G06F 3/1423* (2013.01); *H04N 5/2253* (2013.01); *H04N 5/23299* (2018.08); *H04N 13/239* (2018.05); *H04N 13/25* (2018.05); *A61B 2090/373* (2016.02)

(58) Field of Classification Search
CPC ............. H04N 5/2628; H04N 5/23299; H04N 5/2253; H04N 13/239; H04N 13/25; A61B 90/361; A61B 2090/373; G06F 3/1423

USPC .......................................................... 348/47
See application file for complete search history.

(56) References Cited

U.S. PATENT DOCUMENTS

| | | | | |
|---|---|---|---|---|
| 8,233,052 B2 * | 7/2012 | Augusto | ................ | H04N 5/343 |
| | | | | 348/207.99 |
| 2016/0220324 A1 * | 8/2016 | Tesar | ..................... | A61B 90/25 |
| 2018/0303574 A1 * | 10/2018 | Ramirez Luna | ...... | G06T 19/006 |

FOREIGN PATENT DOCUMENTS

JP 10-323325 A 12/1998

\* cited by examiner

*Primary Examiner* — Matthew K Kwan
(74) *Attorney, Agent, or Firm* — Xsensus LLP

(57) ABSTRACT

A medical observation apparatus includes: a camera including a first imager including a plurality of pixels and configured to image a first medical captured-image in which an observation target is imaged, and a second imager including a plurality of pixels, and configured to image a second medical captured-image in which the observation target is imaged, the second imager including more effective pixels than the first imager; and a display controller configured to cause displays to display the first medical captured-image and an image that corresponds to a region set to the second medical captured-image on a display screen of the respective one of the displays corresponding thereto, wherein one of the first medical captured-image and the second medical captured-image is a medical captured image for a right eye, and another one of the first medical captured-image and the second medical captured-image is a medical captured image for a left eye.

16 Claims, 10 Drawing Sheets

FIG.8
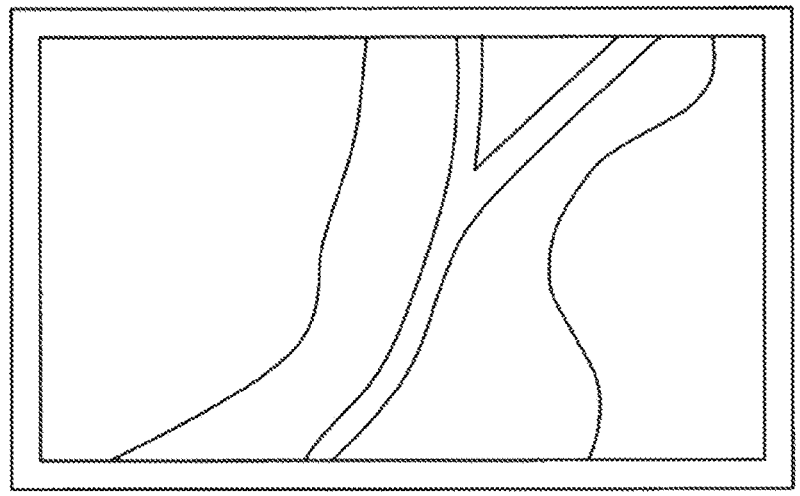
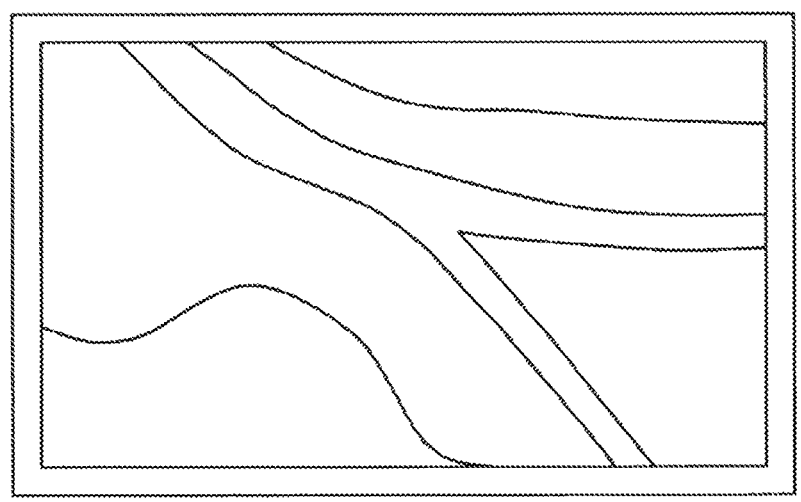
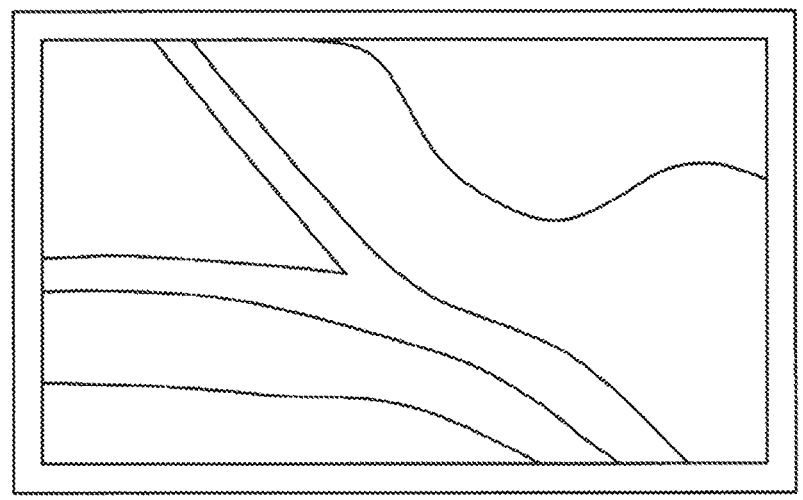

MEDICAL OBSERVATION APPARATUS AND MEDICAL OBSERVATION SYSTEM

The present application claims priority to and incorporates by reference the entire contents of Japanese Patent Application No. 2018-154664 filed in Japan on Aug. 21, 2018.

BACKGROUND

The present disclosure relates to a medical observation apparatus and a medical observation system.

There are cases where medical observation apparatuses that enable to observe an observation target, such as a part to be treated in an enlarged manner are used, for example, to support microsurgery such as neurosurgical operation, or to perform endoscopic surgery in medical sites. The medical observation apparatuses include a medical observation apparatus equipped with an optical microscope, and a medical observation apparatus equipped with an imaging device that has a function as an electronic imaging microscope. Hereinafter, the medical observation apparatus equipped with an optical microscope is referred to as "optical medical-observation apparatus". Moreover, hereinafter, the medical observation apparatus equipped with an imaging device is referred to as "electronic-imaging medical-observation apparatus" or simply "medical observation apparatus". Moreover, hereinafter, a captured image moving image or still image. The same applies hereafter) of an observation target imaged by an imaging device mounted on the medical observation apparatus is referred to as "medical captured image".

In electronic-imaging medical-observation apparatuses, the quality of image of the imaging device has been increasing. Moreover, the quality of image of the display device on which a captured image is displayed has also been increasing. Accordingly, it has become possible to display a medical captured image having as high image quality as that in observation with the optical medical-observation apparatus on a display screen of the display device. Furthermore, it is not necessary for a user (for example, a medical staff, such as an operator and an assistant of the operator. The same applies hereafter) that uses the electronic-imaging medical-observation apparatus to look into an eyepiece instituting an optical microscope as in the case in which the optical medical-observation apparatus is used and, therefore, is possible to change the position of the imaging device flexibly. Thus, use of the electronic-imaging medical-observation apparatus has an advantage of being capable of supporting microsurgery more flexibly, and use of the electronic-imaging medical-observation apparatus in medical sites have been increasing.

In such a situation, a technique of rotating a captured imaged according to an operation to set an angle has been being developed. Examples of the above technique includes the technique disclosed in JP-A-10-323325.

SUMMARY

In an operation in which a medical observation apparatus is used, there is a case in which the operation is performed while more than one medical staff views a medical captured image that is captured by a single imaging device. For example, in an example in which the operation is performed by two medical staffs of the operator (operator surgeon) and an assistant, the display device is arranged in front of both the operator and the assistant. At this time, the up-and-down direction of the imaging device is generally adjusted to match with orientation of the operator.

From the position of the operator, the up-and-down direction of the imaging device, the direction toward which the medical staff faces, and the arrangement direction of the display device match with one another. Therefore, a hand of the operator appears at a lower part of the display screen of the display device that is arranged in front of the operator, and the operator can perform the operation without feeling discomfort.

However, from the position of the assistant, the up-and-down direction of the imaging device, the direction toward which the medical staff faces, and the arrangement direction of the display device do not match one another. Therefore, a hand of the assistant does not appear at a lower part of the display screen of the display device that is arranged in front of the assistant, thereby causing a mismatch between the up-and-down direction in the display screen and the direction toward which the medical staff faces. As a result, intuitive operation by the assistant can be interfered.

As indicated in the above example, in operation in which a medical observation apparatus is used, there is a possibility that part of medical staffs, such as an assistant, cannot perform intuitive operation. Being disabled to perform intuitive operation by using a medical observation apparatus can decrease the convenience of, for example, medical staffs that use the medical observation apparatus.

There is a need for a medical observation apparatus and a medical observation system that improve the convenience of a user that views a display screen on which a medical captured image is displayed.

According to one aspect of the present disclosure, there is provided a medical observation apparatus including: a camera including a first imager including a plurality of pixels and configured to image a first medical captured-image in which an observation target is imaged, and a second imager including a plurality of pixels, and configured to image a second medical captured-image in which the observation target is imaged, the second imager including more effective pixels than the first imager; and a display controller configured to cause displays to display the first medical captured-image and an image that corresponds to a region set to the second medical captured-image on a display screen of the respective one of the displays respectively corresponding thereto, wherein one of the first medical captured-image and the second medical captured-image is a medical captured image for a right eye, and another one of the first medical captured-image and the second medical captured-image is a medical captured image for a left eye.

BRIEF DESCRIPTION OF THE DRAWINGS

FIG. 8 is an explanatory diagram for explaining an example of an image displayed on a display screen of a display device by a first example of processing related to a display control method according to the present embodiment;

DETAILED DESCRIPTION

Hereinafter, exemplary embodiments of the present disclosure are described in detail with reference to the accompanying drawings. Like reference symbols are assigned to like components having practically the same functional configurations throughout the present application and the drawings, and duplicated explanation is thereby omitted.

In the following, it is described in the order below.
1. Medical Observation System According to Present Embodiment and Display Control Method According to Present Embodiment
   [1] Configuration of Medical Observation System
   [1-1] Configuration of Medical Observation System
   [1-2] Functional Configuration of Medical Observation Apparatus
   [2] Processing According to Display Control Method According to Present Embodiment
   [2-1] Overview of Processing According to Display Control Method
   [2-2] First Example of Processing According to Display Control Method
   [2-3] Second Example of Processing According to Display Control Method
   [2-4] Third Example of Processing According to Display Control Method
   [2-5] Fourth Example of Processing According to Display Control Method
   [2-6] Fifth Example of Processing According to Display Control Method
   [3] One Example of Effect Produced by Using Display Control Method According to Present Embodiment (Effect Produced by Using Medical Observation System According to Present Embodiment)
2. Program According to Present Embodiment Medical Observation System According to Present Embodiment and Display Control Method According to Present Embodiment Hereinafter, while describing an example of a medical observation system according to the present embodiment, a display control method according to the present embodiment is described.

In the following, a case in which a medical observation apparatus according to the present embodiment performs a display control method according to the present embodiment, that is, a case in which the medical observation apparatus according to the present embodiment functions as a medical display-control apparatus is mainly described. In the medical observation system according to the present embodiment, an apparatus that functions as the medical display-control apparatus is not limited to the medical observation apparatus according to the present embodiment. For example, in the medical observation system according to the present embodiment, any apparatus that is capable of performing processing related to the display control method according to the present embodiment, such as a medical controller, can function as the medical display-control apparatus.

Figure 1:
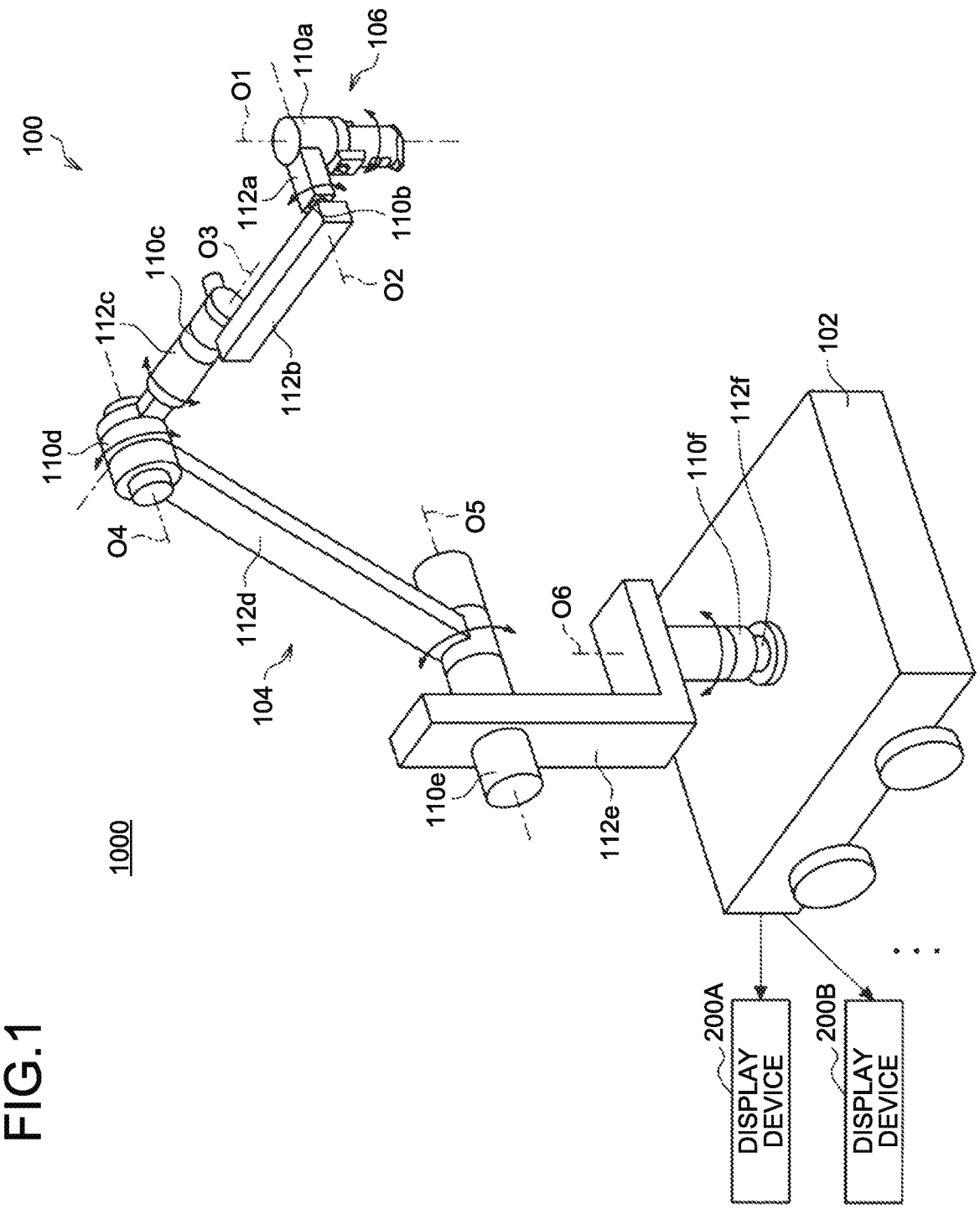
FIG. 1 is an explanatory diagram illustrating an example of a configuration of a medical observation system according to a present embodiment.

[1] Configuration of Medical Observation System
[1-1] Configuration of Medical Observation System FIG. 1 is an explanatory diagram illustrating an example of a configuration of a medical observation system 1000 according to the present embodiment. The medical observation system 1000 illustrated in FIG. 1 includes, for example, a medical observation apparatus 100 and multiple display devices 200A, 200B, . . . . In the following, the multiple display devices 200A, 200B, . . . are collectively, or one of the multiple display devices 200A, 200B, . . . is referred to as "display device 200" in some cases.

Note that the medical observation system according to the present embodiment is not limited to the example illustrated in FIG. 1.

For example, the medical observation system according to the present embodiment may further include a medical control apparatus (not shown) that controls various kinds of operations in the medical observation apparatus 100. The medical observation system 1000 illustrated in FIG. 1 shows an example in which by providing a control unit (described later) in the medical observation apparatus 100, the medical observation apparatus 100 is given the function of the medical control apparatus (not shown) as described later.

Examples of the medical control apparatus (not shown) include a "medical controller", a "computer such as a server", and the like. Moreover, the medical control apparatus (not shown) may be an integrated circuit (IC) that can be incorporated in the device as above.

Furthermore, the medical observation system according to the present embodiment may have a configuration including multiple units of the medical observation apparatuses 100. When the medical observation system according to the present embodiment includes multiple units of the medical observation apparatuses 100, in each of the medical observation apparatuses 100, processing related to the display control method described later is performed. Moreover, when the medical observation system according to the present embodiment has a configuration including multiple units of the medical observation apparatuses 100, each of the medical observation apparatuses 100 is associated with multiple units of the display devices 200. For example, when multiple units of the medical observation apparatuses 100 are associated with a single unit of the display device 200, for example, in the display device 200, a switching operation to switch a medical captured image to be displayed on the display screen is performed, thereby choosing a medical captured image captured by which one of the medical observation apparatuses 100.

Figure 2:
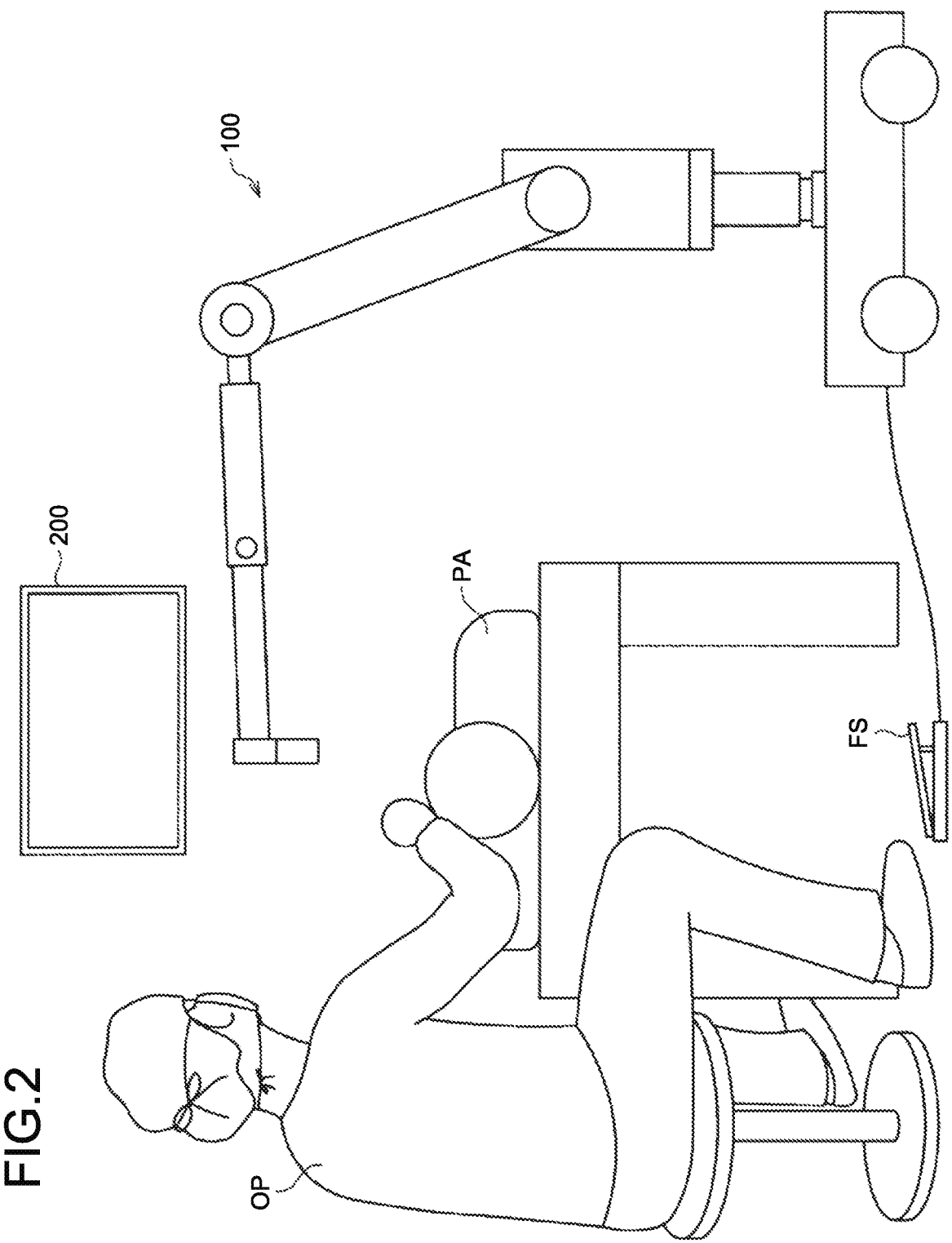
FIG. 2 is an explanatory diagram illustrating an example of a use case in using the medical observation system according to the present embodiment.

FIG. 2 is an explanatory diagram illustrating an example of a use case of the medical observation system 1000 according to the present embodiment, and illustrates an example of the use case in using the medical observation system 1000 according to the present embodiment.

A patient PA (patient subject to medical treatment) being an observation target is imaged by an imaging device (described later) included in the medical observation apparatus 100. A captured image in which a part to be treated (affected part) of the patient PA subjected to the above medical treatment is imaged corresponds to an example of the medical captured image.

The medical captured image captured by the medical observation apparatus 100 is displayed on the display screen of the display device 200. An operator OP that performs the medical treatment by using the medical observation apparatus 100 performs the medical treatment on the patient PA while viewing the medical captured image displayed on the display screen of the display device 200.

Moreover, the operator OP operates an operating device externally provided from the medical observation apparatus 100, such as a foot switch, or an operating device (described later) included in the medical observation apparatus 100, to operate an arm (described later), an imaging device (described later), and the like included in the medical observation apparatus 100, thereby bringing the medical observation apparatus 100 into a desired state.

Although not illustrated in FIG. 2, for example, in neurosurgical operation, it is often the case that an assistant is positioned at a position either on the right or left of the operator OP, and maintains a surgical view or supports the treatment, and the like from a substantially 90° side direction from the operator. When the positional relation between the operator OP and the assistant is as the above example, the display device 200 is arranged in front of each of the operator OP and the assistant, and this causes a situation that the orientation of the display screen of the display device 200 and the orientation of the display screen of the display device 200 that is viewed by the assistant differ by approximately 90°.

Hereinafter, respective apparatuses constituting the medical observation system 1000 according to the present embodiment illustrated in FIG. 1 are described.

[1-1-1] Display Device 200

The display device 200 is a display unit in the medical observation system 1000 according to the present embodiment, and corresponds to an external display device from the medical observation apparatus 100. The display device 200 displays various images, such as a medical captured image captured by the medical observation apparatus 100 and an image related to a user interface (UI), on the display screen. Moreover, the display device 200 may have a configuration enabling 3D display by an arbitrary method. Display in the display device 200 is controlled by, for example, the medical observation apparatus 100 or a medical control apparatus (not shown).

The display device 200 is arranged at an arbitrary position, such as on a wall, a ceiling, and a floor of an operating room, viewable for a person that is involved in an operation, such as an operator, in the operating room in the medical observation system 1000.

Examples of the display device 200 include a liquid crystal display, an organic electroluminescence (EL) display, a cathode ray tube (CRT) display, and the like.

Note that the display device 200 is not limited to the above examples. For example, the display device 200 may be an arbitrary wearable device that is used, being worn on operator's body, such as a head-mount display and an eyewear type display.

The display device 200 is actuated by power supplied by an internal power source, such as a battery provided in the display device 200, or by power supplied from an external power source connected thereto.

[1-1-2] Medical Observation Apparatus 100

The medical observation apparatus 100 is an electronic-imaging medical-observation apparatus. For example, when the medical observation apparatus 100 is used at operation, an operator observes a part to be treated, while viewing a medical captured image that is captured by the medical observation apparatus 100 and that is displayed on the display screen of the display device 200, and performs various kinds of treatment, such as procedure according to operation, with respect to the part to be treated.

As illustrated in FIG. 1, the medical observation apparatus 100 includes, for example, a base 102, an arm 104, and an imaging device unit 106.

Moreover, although not illustrated in FIG. 1, the medical observation apparatus 100 may include, for example, one or more processors (not shown) that is constituted of an arithmetic circuit, such as a micro processing unit (MPU), a read only memory (ROM) (not shown), a random access memory (RAM) (not shown), a recording medium (not shown), and a communication device (not shown). The medical observation apparatus 100 is actuated by power supplied from an internal power source, such as a battery provided in the medical observation apparatus 100, by power supplied from an external power source connected thereto, or the like.

The processor (not shown) functions as a control unit (described later) in the medical observation apparatus 100. The ROM (not shown) stores control data, such as a program and arithmetic parameters, used by the processor (not shown). The RAM (not shown) temporarily stores a program executed by the processor (not shown), and the like.

The recording medium (not shown) functions as a storage unit (not shown) in the medical observation apparatus 100. The recording medium (not shown) stores various kinds of data, such as data related to the display control method according to the present embodiment and various kinds of applications. Examples of the recording medium (not shown) include a magnetic recording medium such as a hard disk, a non-volatile memory such as a flash memory, and the like. Furthermore, the recording medium (not shown) may be detachable from the medical observation apparatus 100.

The communication device (not shown) is a communication unit included in the medical observation apparatus 100, and plays a role in communicating with an external device, such as the display device 200, in a wireless or wired manner. Examples of the communication device (not shown) include an IEEE 802.15.1 port and a transceiving circuit (wireless communication), an IEEE 802.11 port and a transceiving circuit (wireless communication), a communication antenna and a radio frequency (RF) circuit wireless communication), a local area network (LAN) terminal and a transceiving circuit (wired communication), and the like.

[1-1-2-1] Base 102

The base 102 is a base of the medical observation apparatus 100, and one end of the arm 104 is connected thereto. The base 102 supports the arm 104 and the imaging device unit 106.

Moreover, for example, casters are provided in the base 102, and the medical observation apparatus 100 stands on the floor through the casters. By providing casters, the medical observation apparatus 100 is enabled to be moved easily on the floor with the casters.

[1-1-2-2] Arm 104

The arm 104 is structured with plural links connected one another by joints.

The arm 104 supports the imaging device unit 106. The imaging device unit 106 supported by the arm 104 is three-dimensionally movable, and the imaging device unit 106 after a move is held by the arm 104 to maintain the position and the orientation.

More specifically, the arm 104 includes, for example, plural joints 110a, 110b, 110c, 110d, 110e, 110f, and plural links 112a, 112b, 112c, 112d, 112e, 112f that are rotatably joined one another by the joints 110a, 110b, 110c, 110d, 110e, 110f.

That is, in the medical observation apparatus 100 illustrated in FIG. 1, by six rotation axes (a first axis O1, a second axis O2, a third axis O3, a fourth axis O4, a fifth axis O5, and a sixth axis O6) corresponding to the six joints 110a, 110b, 110c, 110d, 110e, 110f constituting the arm 104, six degrees of freedom in movement of the imaging device unit 106 is realized. More specifically, in the medical observation apparatus 100 illustrated in FIG. 1, movement in six degrees of freedom, consisting of three degrees of freedom in translation and three degree of freedom in rotation, is realized.

An actuator (not shown) may be arranged in some of all of the joints 110a, 110b, 110c, 110d, 110e, 110f. When the actuator (not shown) is arranged, the joint in which the actuator is arranged rotates about a corresponding rotation axis by a driving force of the actuator. The driving force of the actuator (not shown) is controlled by, for example, a processor that functions as a control unit described later, or by an external medical control apparatus (not shown).

When the actuator (not shown) is arranged, various movements of the arm 104, such as stretching and bending (folding) of the arm 104, are realized as each of the joints 110a, 110b, 110c, 110d, 110e, 110f rotates about the corresponding rotation axis by the driving force of the actuator.

To each of the joints 110a, 110b, 110c, 110d, 110e, 110f, an angle sensor (not shown) that is capable of detecting a rotation angle of each of six rotation axes may be provided. As described later, when the angle sensor (not shown) is provided, a change of position and a change of orientation of the imaging device unit 106 can be detected by using the angle sensor. Examples of the angle sensor (not shown) include any sensor that is capable of acquiring a rotation axis at each of the six rotation axes, such as a rotary encoder and an angular velocity sensor.

The joint 110a has a substantially cylindrical shape, and supports the imaging device unit 106 (an upper end portion of the imaging device unit 106 in FIG. 1) so as to be rotatable about a rotation axis (the first axis O1) parallel to a center axis of the imaging device unit 106 at an end portion (a lower end portion in FIG. 1) of the joint 110a. The medical observation apparatus 100 is configured such that the first axis O1 illustrated in FIG. 1 coincides with an optical axis in the imaging device unit 106. That is, by rotating the imaging device unit 106 about the first axis O1 in FIG. 1, a medical captured image captured by the imaging device unit 106 is to be an image, a field of view of which is changed as rotating.

The link 112a is a substantially rod-shaped member, and supports the joint 110a in a fixed manner. The link 112a extends, for example, in a direction perpendicular to the first axis O1, and is connected to the joint 110b.

The joint 110b has a substantially cylindrical shape, and supports the link 112a so as to be rotatable about a rotation axis (the second axis O2) perpendicular to the first axis O1. Moreover, to the joint 110b, the link 112b is connected in a fixed manner.

The link 112b is a substantially rod-shaped member, and extends in a direction perpendicular to the second axis O2. Moreover, to the link 112b, the joint 110b and the joint 110c are both connected.

The joint 110c has a substantially cylindrical shape, and supports the link 112b so as to be rotatable about a rotation axis (the third axis O3) perpendicular to each of the first axis O1 and the second axis O2. Moreover, to the link 110c, one end of the link 112c is connected in a fixed manner.

As a distal end side (side on which the imaging device unit 106 is arranged) of the arm 104 rotates about the second axis O2 and the third axis O3, it is possible to move the imaging device unit 106 such that the position of the imaging device unit 106 is changed in a horizontal plane. That is, in the medical observation apparatus 100, by controlling rotation about the second axis O2 and the third axis O3, a field of view of a medical captured image can be moved in a plane.

The link 112c is a member that has a substantially cylindrical shape at one end, and has a substantially rod shape at the other end. To one end of the link 112c, the joint 110c is connected in a fixed manner such that a center axis of the joint 110c and a center axis of the substantially cylindrical shape coincide with each other. Furthermore, to the other end of the link 112c, the joint 110d is connected.

The joint 110d has a substantially cylindrical shape, and supports the link 112c so as to be rotatable about a rotation axis (the fourth axis O4) perpendicular to the third axis O3. To the joint 110d, and the link 112d is connected.

The link 112d is a substantially rod-shaped member, and extends in a direction perpendicular to the fourth axis O4. One end of the link 112d is connected to the joint 110d in a fixed manner so as to abut on a side surface of the substantially cylindrical shape of the joint 110d. Moreover, the other end of the link 112d (opposite side to the side on which the joint 110d is connected), the joint 110e is connected.

The joint 110e has a substantially cylindrical shape, and supports one end of the link 112d so as to be rotatable about a rotation axis (the fifth axis O5) parallel to the fourth axis O4. Moreover, to the joint 110e, one end of the link 112e is connected in a fixed manner.

The fourth axis O4 and the fifth axis O5 are rotation axes that are capable of moving the imaging device unit 106 in a vertical direction. As the distal end side (side on which the imaging device unit 106 is arranged) of the arm 104 rotates about the fourth axis O4 and the fifth axis O5, the position of the imaging device unit 106 in a vertical direction changes. Accordingly, as the distal end side (side on which the imaging device unit 106 is arranged) of the arm 104 rotates about the fourth O4 and the fifth axis O5, a distance between the imaging device unit 106 and an observation target, such as a part to be treated of a patient, can be changed.

The link 112e is a member structured by combining a first member that has a substantially L-shape with one side extending in a vertical direction and the other side extending in a horizontal direction, and a second member that has a rod shape extending downward in a vertical direction from a portion of the first member that extends in a horizontal direction. To a portion that extends in a vertical direction of the first member of the link 112e, the joint 110e is connected in a fixed manner. Moreover, to the second member of the link 112e, the joint 110f is connected.

The joint 110f has a substantially cylindrical shape, and supports the link 112e so as to be rotatable about a rotation axis (the sixth axis O6) parallel to the vertical direction. Furthermore, to the joint 110f, the link 112f is connected in fixed manner.

The link 112f is a substantially a rod-shaped member, and extends in a vertical direction. To one end of the link 112f, the joint 110f is connected. Moreover, the other end (end on an opposite side to the side on which the joint 110f is connected) of the link 112f is connected to the base 102 in a fixed manner.

Because the arm 104 has the structure as described above, six degrees of freedom in movement of the imaging device unit 106 is realized in the medical observation apparatus 100.

Note that the structure of the arm 104 is not limited to the example described above.

For example, in each of the joints 110a, 110b, 110c, 110d, 110e, 110f, a break to control rotation at each of the joints 110a, 110b, 110c, 110d, 110e, 110f may be further arranged. Examples of the break according to the present embodiment include any type of break, such as a brake that drives mechanically and an electromagnetic break that drives electrically.

Actuation of the break is controlled, for example, by a processor that functions as a control unit described later, or an external medical control apparatus (not shown). As the actuation of the break is controlled, an operation mode of the arm 104 is set in the medical observation apparatus 100. The operation mode of the arm 104 includes, for example, a fixed mode and a free mode.

The fixed mode (second operation mode) according to the present embodiment is an operation mode in which the position and the orientation of the imaging device unit 106 (the position and the orientation of an imaging unit 150 described later) are fixed by restricting rotation at each rotation axis in the arm 104 by the break. When it is in the fixed mode, even if an actuator is provided in some of or all of the joints 110a, 110b, 110c, 110d, 110e, 110f, the actuator does not operate. When the arm 104 is turned into the fixed mode, an operating state of the medical observation apparatus 100 is turned into a fixed state in which the position and the orientation of the imaging device unit 106 are fixed.

Moreover, the free mode (first operation mode) according to the present embodiment is an operation mode in which each of the rotation axes in the arm 104 is freely rotatable by releasing the break. When it is in the free mode, and when the actuator is provided in some of or all of the joints 110a, 110b, 110c, 110d, 110e, 110f, the actuator operates. Moreover, for example, when the actuator is not provided in the respective joints 110a, 110b, 110c, 110d, 110e, 110f, the position and the orientation of the imaging device unit 106 (the position and the orientation of the imaging unit 150 described later) can be adjusted by direct operation by an operator in the free mode. When the actuator is provided in some of or all of the joints 110a, 110b, 110c, 110d, 110e, 110f also, the position and the orientation of the imaging device unit 106 may adjustable by direct operation by an operator in the free mode. The direction operation according to the present embodiment is, for example, operation of an operator holding the imaging device unit 106 with a hand and of directly moving the imaging device unit 106.

[1-1-2-3] Imaging Device Unit 106

The imaging device unit 106 is supported by the arm 104. The imaging device unit 106 includes at least two imaging devices that function as a stereo camera, and images an observation target, such as a part to be treated of a patient, by the respective imaging devices. That is, the imaging devices included in the imaging device unit 106 are supported by the arm 104. Imaging by the imaging devices included in the imaging device unit 106 is controlled by, for example a processor that functions as a control unit described later, or an external medical control apparatus (not shown). Hereinafter, imaging by the imaging devices included in the imaging device unit 106 can be referred to as "imaging by the imaging device unit 106" in some cases.

In the following, a case in which the imaging device unit 106 includes two imaging devices of a first imaging device and a second imaging device that function as a stereo camera is described as an example. The first imaging device has multiple pixels, and acquires a medical captured image in which an observation target is imaged. The second imaging device has multiple pixels including more effective pixels than the firs imaging device, and acquires a medical captured image in which an observation target is imaged. The effective pixels are pixels that are used for imaging a medical captured image out of the multiple pixels of the first imaging device and the second imaging device. Generally, the number of effective pixels is smaller than the actual number of pixels (hereinafter, "the total number of pixels") respectively in the first imaging device and the second imaging device, but the number of effective pixels and the total number of pixels may be the same. As described above, the first imaging device and the second imaging device have different number of effective pixels. On the other hand, the total number of pixels in the first imaging device and the total number of pixels of the second imaging device may be the same or be different. The total number of pixels being different between the first imaging device and the second imaging device includes that the total number of pixels in the second imaging device is larger than the total number of pixels in the first imaging device, and that the total number of pixels in the first imaging device is larger than the total number of pixels in the second imaging device. In the following, a medical captured image acquired by the first imaging device is referred to as "first medical captured image", and a medical captured-image acquired by the second imaging device is referred to as "second medical captured-image". Because the first imaging device and the second imaging device function as a stereo camera, one of the first medical captured-image and the second medical captured-image is a medical captured image for a right eye. Moreover, the other one of the first medical captured-image and the second medical captured-image is a medical captured image for a left eye. An example of the pixels of the first imaging device and the pixels of the second imaging device is described later.

Respective imaging devices included in the imaging device unit 106 have a configuration, for example, corresponding to an electronic imaging microscope.

Figure 3:
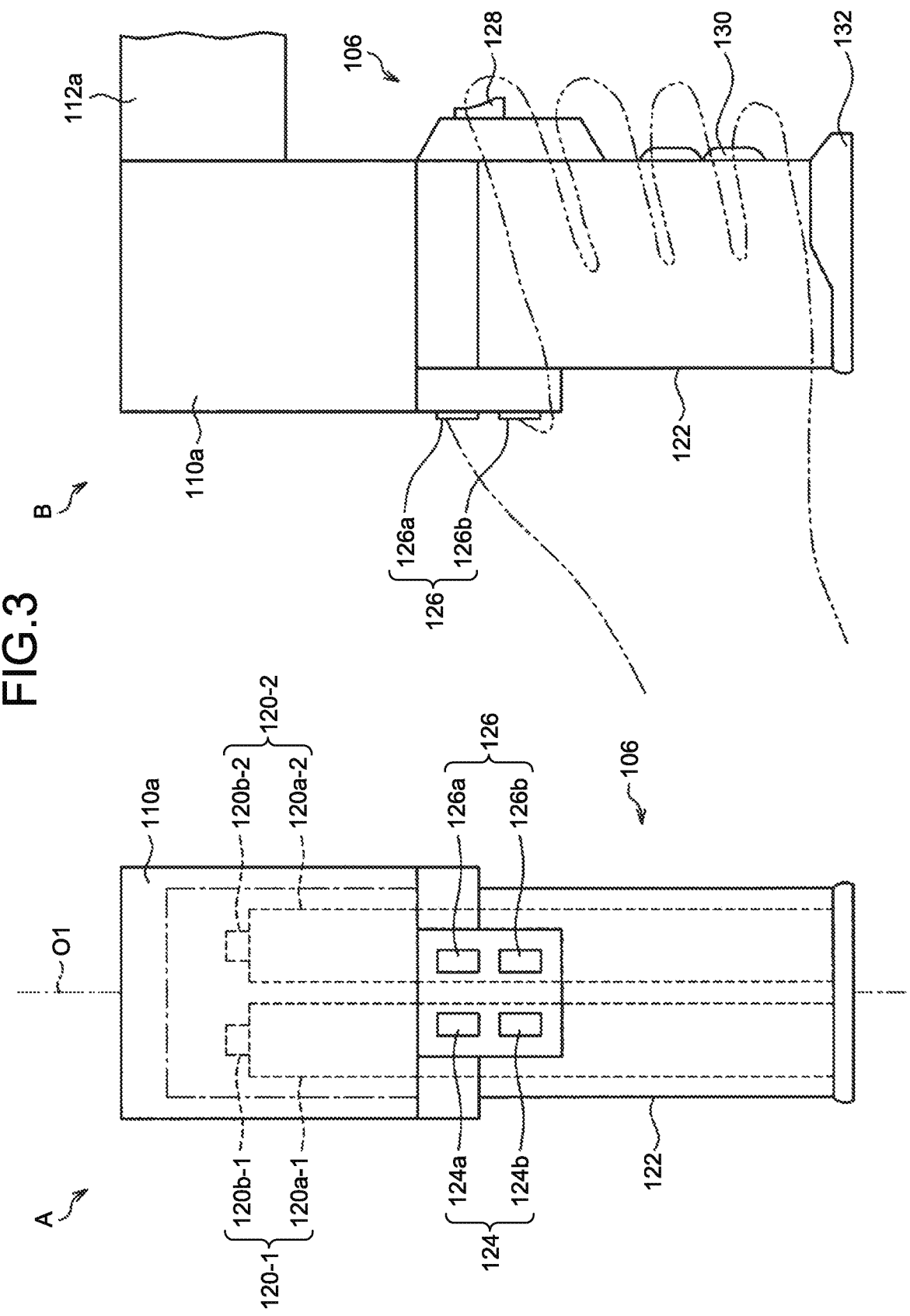
FIG. 3 is an explanatory diagram for explaining an example of a configuration of an imaging device included in a medical observation apparatus according to the present embodiment.

FIG. 3 is an explanatory diagram for explaining an example of a configuration of the imaging device unit 106 included in the medical observation apparatus 100 according to the present embodiment.

The imaging device unit 106 includes, for example, a first imaging device 120-1, a second imaging device 120-2, and a tubular member 122 having a substantially tubular shape. The first imaging device 120-1 and the second imaging device 120-2 are arranged in the tubular member 122.

On an opening at a lower end (end on a lower side in FIG. 3) of the tubular member 122, a cover glass (not shown) to protect the first imaging device 120-1 and the second imaging device 120-2 is arranged.

Moreover, for example, a light source (not shown) is arranged inside the tubular member 122, and illumination light is irradiated to a subject through the cover glass from the light source at imaging. As reflected light (observation light) from the subject on which the illumination light has been irradiated enters each of the first imaging device 120-1 and the second imaging device 120-2 through the cover glass (not shown), an image signal expressing the subject (image signal expressing a medical captured image) is acquired respectively by the first imaging device 120-1 and the second imaging device 120-2.

As each of the first imaging device 120-1 and the second imaging device 120-2, a configuration used in various kinds of publicly-known electronic imaging microscope unit can be applied.

As an example, in the first imaging device 120-1 is constituted of, for example, an optical system 120a-1 and an image sensor 120b-1 that includes pixels for imaging an image of an observation target by light that has passed through the optical system 120a-1. Moreover, the second imaging device 120-2 is constituted of, for example, an optical system 120a-2, and an image sensor 120b-2 that includes pixels for imaging an image of an observation target by light that has passed through the optical system 120a-2. Each of the optical systems 120a-1 and the optical system 120a-2 is constituted of optical devices including, for example, one or more lenses, such as an objective lens, a zoom lens, and a focus lens, and a mirror. Examples of the image sensor 120b-1 and the image sensor 120b-2 includes, for example, an image sensor using multiple pixels (imaging devices), such as a complementary metal oxide semiconductor (CMOS) and a charge coupled device (CCD).

Each of the image sensor 120b-1 and the image sensor 120b-2 may have as many pixels as to enable so-called high resolution imaging. By respectively configuring the first imaging device 120-1 and the second imaging device 120-2 to be capable of high resolution imaging, it becomes possible to display an image on the display device 200 having a large display screen of, for example, 50 inches or larger while keeping a certain resolution (for example, full high-definition (HD) image), and the visibility for a viewer of the display screen is thus improved. Moreover, respectively configuring the first imaging device 120-1 and the second imaging device 120-2 to be capable of high resolution imaging, even if a captured image is enlarged by an electronic zoom function to be displayed on the display screen of the display device 200, a certain resolution is kept. Furthermore, when a certain resolution is kept using the electronic zoom function, specifications of an optical zoom function in each of the first imaging device 120-1 and the second imaging device 120-2 can be reduced and, therefore, the optical systems of the first imaging device 120-1 and the second imaging device 120-2 can be configured further simply. Moreover, as the optical systems of the first imaging device 120-1 and the second imaging device 120-2 become further simple, it becomes possible to make the imaging device unit 106 more compact.

FIG. 3 illustrates an example in which the imaging device unit 106 includes the independent first imaging device 120-1 and second imaging device 120-2. Note that the optical systems of the first imaging device 120-1 and the second imaging device 120-2 may be a Galileo optical system, at least part of which is shared.

The first imaging device 120-1 and the second imaging device 120-2 respectively have one or more functions that are generally equipped with an electronic imaging microscope, such as a zoom function (one or both of an optical zoom function and an electronic zoom function) and an auto focus (AF) function.

In the imaging device unit 106, for example, various kinds of operating devices to control operation of the imaging device unit 106 are arranged. For example, in the example in FIG. 3, a zoom switch 124, a focus switch 126, and an operation-mode changing switch 128 are provided in the imaging device unit 106. It is needless to say that positions and forms in which the zoom switch 124, the focus switch 126, and the operation-mode changing switch 128 are arranged are not limited to the example illustrated in FIG. 3.

The zoom switch 124 and the focus switch 126 are an example of the operating device to adjust an imaging condition in the imaging device unit 106.

The zoom switch 124 includes, for example, a zoom-in switch 124a that increases a zoom factor (magnification), and a zoom-out switch 124b that reduces a zoom factor. When the zoom switch 124 is operated, the zoom factor is adjusted, and zoom is adjusted.

The focus switch 126 includes, for example, a wide-range focus switch 126a by which a focal length to an observation target (subject) is increased, and a close-range focus switch 126b by which a focal length observation target is decreased. By operating the focus switch 126, the focal length is adjusted, and the focus is adjusted.

The operation-mode changing switch 128 is an example of an operating device to change the operation mode of the arm 104 in the imaging device unit 106. By operating the operation-mode changing switch 128, the operation mode of the arm 104 is changed. The operation mode of the arm 104 includes, for example, the fixed mode and the free mode as described above.

An example of operation with respect to the operation-mode changing switch 128 includes operation of pressing the operation-mode changing switch 128. For example, during an operator presses the operation-mode changing switch 128, the operation mode of the arm 104 is in the free mode, and when the operation is not pressing the operation-mode changing switch 128, the operation mode of the arm 104 is in the fixed mode.

Furthermore, to improve the operability and the convenience at the time when an operator that performs operation with respect to the respective operating devices performs operation, for example, a non-slip member 130 and a projecting member 132 are arranged in the imaging device unit 106.

The non-slip member 130 is a member arranged to avoid slipping of an operating body, for example, at the time when the operator operates the tubular member 122 with the operating body, such as a hand.

The projecting member 132 is a member arranged to prevent the field of view of the respective optical system 120a-1 and optical system 120a-2 from being blocked, for example, when the operator operates the tubular member 122 with an operating body, such as a hand, or to prevent the cover glass (not shown) from getting dirty by the operating body touching the cover glass when operation is performed with the operating body.

It is needless to say that the position and a form in which the non-slip member 130 and the projecting member 132 are arranged are not limited to the example illustrated in FIG. 3. Moreover, in the imaging device unit 106, one or both of the non-slip member 130 and the projecting member 132 may be absent.

An image signal (image data) that is generated by imaging by the imaging device unit 106 is subjected to image processing, for example, by a processor functioning as a control unit described later. The image processing according to the present embodiment includes, for example, one or more kinds of processing out of various kinds of processing, such as gamma correction, white balance adjustment, enlargement and reduction by the electronic zoom function, inter-pixel correction, processing of cutting out part of an image, and rotation processing of rotating an image.

Note that when the medical observation system according to the present embodiment includes a medical control apparatus (not shown) that controls various kinds of operations in the medical observation apparatus 100, the image processing according to the present embodiment may be performed in the medical control apparatus.

The medical observation apparatus 100 transmits, for example, a display control signal and an image signal subjected to the image processing as described above to the display device 200.

As the display control signal and the image signal are transmitted to the display device 200, the a medical captured image in which an observation target is imaged (for example, a captured image in which a part to be treated is imaged) is displayed on the display screen of the display device 200.

The medical observation apparatus 100 illustrated in FIG. 1 has, for example, a hardware configuration described referring to FIG. 1 and FIG. 3.

The hardware configuration of the medical observation apparatus according to the present embodiment is not limited to the configuration described referring to FIG. 1 and FIG. 3.

For example, the medical observation apparatus according to the present embodiment may have a configuration in which the arm 104 is directly attached to a ceiling or a wall of an operation room, without the base 102. For example, when the arm 104 is attached to a ceiling, the medical observation apparatus according to the present embodiment has a configuration in which the arm 104 is hang from the ceiling.

Moreover, the example in which the arm 104 is configured to realize six degrees of freedom in driving of the imaging device unit 106 is illustrated in FIG. 1, but the configuration of the arm 104 is not limited to the configuration with which the imaging device unit 106 has six degrees of freedom in driving. For example, as long as the arm 104 is configured to be able to move the imaging device unit 106 appropriately according to a use, the number and arrangement of joints and links, the direction of driving axes of the joints, and the like can be set appropriately to give desired freedom to the arm 104.

Furthermore, the example in which various kinds of operating devices to control operation of the imaging device unit 106 are provided in the imaging device unit 106 is illustrated in FIG. 1 and FIG. 3, but some of or all of the operating devices illustrated in FIG. 1 and FIG. 3 may be excluded to be provided in the imaging device unit 106. As an example, various kinds of operating devices to control operation of the imaging device unit 106 may be arranged in a part other than the imaging device unit 106 constituting the medical observation apparatus according to the present embodiment, as another example, various kinds of respective operating devices to control operation of the imaging device unit 106 may be an external operating device, such as a foot switch FS and a remote controller.

Moreover, the imaging device unit 106 may be configured to be able to switch among multiple observation modes. The observation mode according to the present embodiment includes, for example, an observation mode in which imaging is performed with available light, an observation mode in which imaging is performed with special light, an observation mode in which imaging is performed using an image enhancement observation technique, and the like. The special light according to the present embodiment is, for example, light in a specific wavelength range, such as light of a near infrared wavelength range, and light of a fluorescence wavelength range in fluorescence observation using 5-aminolevulinic acid (5-ALA).

An example of configuration of the imaging device unit 106 in which the observation modes can be switched includes, for example, a "configuration in which a filter that passes light of a specific wavelength range, and that does not pass light of other wavelength range, and a moving mechanism that selectively arranges the filter on an optical path are provided in each of the first imaging device 120-1 and the second imaging device 120-2". Examples of the specific wavelength range to be passed through the filter according to the present embodiment include a near infrared wavelength range (for example, a wavelength range of approximately 0.7 micrometers to 2.5 micrometers), a fluorescence wavelength range by fluorescence observation using 5-ALA (for example, a wavelength range of approximately 0.6 micrometers to 0.65 micrometers), a fluorescence wavelength range of indocyanine green (ICG) (for example, a wavelength range of approximately 0.82 micrometers to 0.85 micrometers), and the like.

Note that multiple filters that pass light of different wavelength range may be provided in the respective first imaging device 120-1 and second imaging device 120-2. Moreover, the example in which imaging is performed with light of a specific wavelength range by arranging a filter on an optical path has been described in the above, but it is needless to say that respective configurations of the first imaging device 120-1 and the second imaging device 120-2 to perform imaging with light of a specific wavelength range are not limited to the example described above.

Other examples of the imaging device unit 106 are described later.

[1-2] Functional Configuration of Medical Observation Apparatus 100

Figure 4:
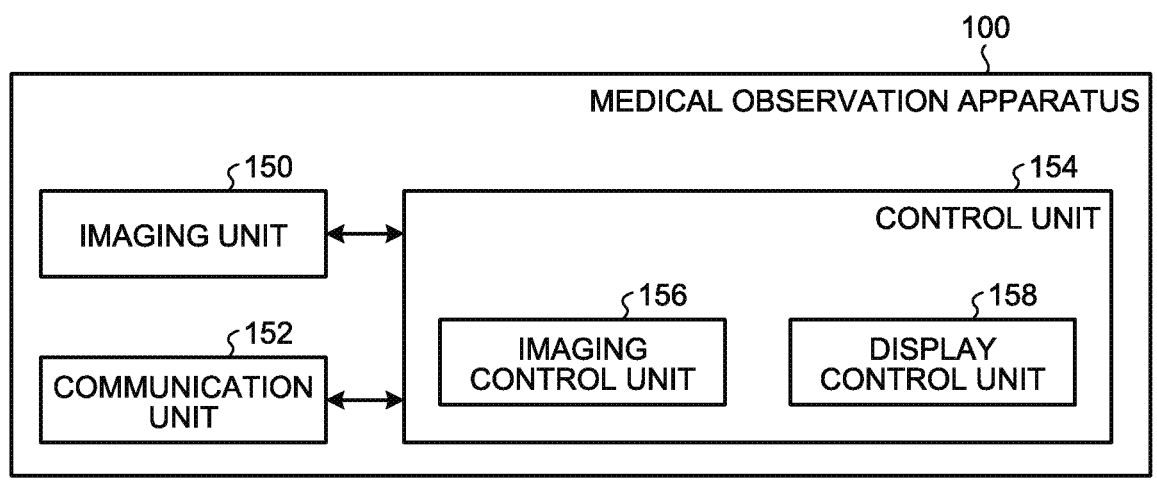
FIG. 4 is a functional block diagram illustrating an example of the configuration of the medical observation apparatus according to the present embodiment.

Next, the medical observation apparatus 100 illustrated in FIG. 1 is described using a functional blocks. FIG. 4 is a functional block diagram illustrating an example of the configuration of the medical observation apparatus 100 according to the present embodiment.

The medical observation apparatus 100 includes, for example, the imaging unit 150, a communication unit 152, and a control unit 154.

The imaging unit 150 images an observation target. The imaging unit 150 is constituted of, for example, the imaging device 120-1 and the second imaging device 120-2. As described above, by imaging by the first imaging device 120-1, the first medical captured image is acquired and by imaging by the second imaging device 120-2, the second medical captured image is acquired. Moreover, as described above, one of the first medical captured-image and the second medical captured-image is a medical captured image for right eye, and the other one is a medical captured image for left eye. Imaging in the imaging unit 150 is controlled by, for example, the control unit 154.

The communication unit 152 is a communication unit that is included in the medical observation apparatus 100, and plays a role in performing communication with an external device, such as the display device 200, by wireless or wired communication. The communication unit 152 is constituted of, for example, the communication device (not shown) described above. Communication in the communication unit 152 is controlled by, for example, the control unit 154.

The control unit 154 is constituted of, for example, the processor (not shown) described above, and plays a role in controlling the entire medical observation apparatus 100. Moreover, the control unit 154 plays a role in leading to perform processing related to the display control method described later. Note that processing related to the display control method described later in the control unit 154 may be performed, distributed to multiple processing circuits (for example, multiple processors, and the like).

More specifically, the control unit 154 has, for example, an imaging control unit 156 and a display control unit 158.

The imaging control unit 156 controls the imaging devices constituting the imaging unit 150. Examples of the control of the imaging devices include control of one or more functions generally provided in an electronic-imaging microscope, such as the zoom function (an optical zoom function and an electronic zoom function) and the AF function.

The display control unit 158 performs processing related to the display control method according to the present embodiment, and controls display of a medical captured image on the display screen. The display control unit 159 transmits, for example, a display control signal and an image signal to the communication device (not shown) constituting the communication unit 152, to cause it to transmit the display control signal and the image signal to the display device 200, thereby controlling display in the display device 200. Note that control of communication in the communication unit 152 may be performed by a communication control unit (not show constituting the control unit 154.

Examples of control of display of a medical captured image on the display screen in the display control unit 158 include "processing of changing the display device 200 on which the medical captured image is displayed according to a medical captured image to be displayed". As described later, the display control unit 158 can perform control (control of 3D display) of displaying respective medical captured image for right eye and medical captured image for left eye on the display screen.

The medical captured image to be displayed according to the present embodiment includes images described below.

The first medical captured-image (a medical captured image in which an observation target is imaged by the first imaging device 120-1. The same applies hereafter)

An image corresponding to a "region set with respect to the second medical captured-image (a medical captured image in which an observation target is imaged by the second imaging device 120-2. The same applies hereafter)

As described above, one of the first medical captured-image and the second medical captured-image is a medical captured image for right eye, and the other is a medical captured image for left eye. Furthermore, as described above, the second imaging device 120-2 has more effective pixels than the first imaging device 120-1 and, therefore, the size of the second medical captured-image is larger than the size of the first medical captured-image. As in an example described later, by setting a region with respect to the second medical captured-image, the size of an image corresponding to the region can be adjusted to the size corresponding to the first medical captured-image. The image in the size corresponding to the first medical captured-image herein includes, for example, an "image in the same size as the first medical captured-image" and an "image that can be recognized as in the same size as the first medical captured-image by a person viewing the image". In the following, a case in which an image corresponding to a region set with respect to the second medical captured-image is an image in the same size as the first medical captured-image is described as an example.

Different regions set with respect to the second medical captured-image include, for example, one or both of a "region (hereinafter, it can be referred to as "first region") in which an imaging range with respect to an observation target is the same as the first medical captured-image", and a "region obtained by rotating the first region". Although not referring in detail in the following, because the first region is a region set with respect to the second medical captured-image, an image corresponding to the first region corresponds to part of the second medical captured-image. Moreover, although not referring in detail in the following, an image corresponding to the other region set with respect to the second medical captured-image also (region other than the first region) corresponds to part of the second medical captured-image similarly.

Specifically, the display control unit 158 causes a first display device to display the first medical captured-image, or causes the first display device to display the first medical captured-image and an image corresponding to the first region as a stereoscopic image. A case in which the first medical captured-image is displayed on the first display device corresponds to a case in which a 2D image is displayed on a display screen of the first display device. Furthermore, a case in which the first medical captured-image and the image corresponding to the first region are displayed on the display screen of the display device corresponds to a case in which a 3D image is displayed on the display screen of the first display device.

The first display device according to the present embodiment is, for example, the display device 200, the arrangement direction of which matches with the up-and-down direction of the imaging device. In the medical observation system 1000, the first display device corresponds to, for example, the display device 200 that is set as a default display device. The first display device is, for example, the display device 200 that is viewed by an operator. Note that the example of the first display device is not limited to the above. For example, the first display device according to the present embodiment may include the display device 200, the orientation of the display screen of which is the same as that the display device 200 (an example of the default display device) that is viewed by the operator. The orientation of the display screen being the same according to the present embodiment includes a case in which an angle formed by a direction of a perpendicular line of one display screen and a direction of a perpendicular line of another display screen is 0°, and a case in which the angle is 0+E1[°] (E1 is, for example, a "rational number corresponding to an allowable error that is set at a design stage or the like").

Moreover, the display control unit 158 displays an image corresponding to the first region (an example of an image corresponding to a region that is set with respect to the second medical captured-image), or an image corresponding to a region obtained by rotating the first region (another example of an image corresponding to a region that is set with respect to the second medical captured-image) on a display screen of a second display device. The image displayed on the second display device is an image that is obtained by rotating the image corresponding to the region that is obtained by rotating the first region, so as to be suitable for the second display device. By display the image rotated so as to be suitable for the second display as described above, an image, the up-and-down direction and the left-and-right direction of which match with those from a position of a viewer of an image displayed on the second display device can be displayed on the display screen of the second display device.

The second display device according to the present embodiment is the display device 200 that is different from the first display device, and is the display device 200, the orientation of the display screen of which can be different from the first display device. Examples of the second display device includes the display device 200 that is viewed by, for example, an assistant. It is needless to say that the second display device is not limited to the example described above. Hereinafter, an image corresponding to a region that is set with respect to the second medical captured-image can be referred to simply as "image corresponding to a region".

An example of the image corresponding to a region and an example of display of the image corresponding to a region are described later.

Having the display control unit 158, the control unit 154 plays a role in leading to perform processing related to the display control method according to the present embodiment. Moreover, having the imaging control unit 156 and the display control unit 158, the control unit 154 plays a role in controlling the entire medical observation apparatus 100.

Note that the functional configuration of the control unit 154 is not limited to the example illustrated in FIG. 4.

For example, the control unit 154 may have an arbitrary configuration according to separation of the functions of the medical observation apparatus 100, such as a configuration according to separation of processing related to the display control method according to the present embodiment.

As an example, when the medical observation apparatus 100 has the configuration as illustrated in FIG. 1, the control unit 154 may further include an arm control unit (not shown) that controls actuation of the arm 104. Examples of the control of actuation of the arm 104 include "application of a control signal to control actuation to the actuators that respectively correspond to the joints 110a, 110b, 110c, 110d, 110e, 110f" when the actuators (not shown) are provided in some of or all of the joints 110a, 110b, 110c, 110d, 110e, 110f, and the like.

The medical observation apparatus 100 performs the processing related to the display control method according to the present embodiment, for example, by the functional configuration illustrated in FIG. 4.

The functional configuration of the medical observation apparatus is not limited to the configuration illustrated in FIG. 4.

For example, the medical observation apparatus according to the present embodiment includes, one or both of the imaging control unit 156 and the display control unit 158 illustrated in FIG. 4, independently from the control unit 154 (for example, implemented by separate processing circuits).

Moreover, the functional configuration that enable to perform the processing related to the display control method according to the present embodiment in the medical observation apparatus according to the present embodiment is not limited to the configuration illustrated in FIG. 4. For example, the medical observation apparatus according to the present embodiment can take a functional configuration according to separation of the processing related to the display control method according to the present embodiment.

Furthermore, when the medical observation apparatus according to the present embodiment has the configuration illustrated in FIG. 1, the medical observation apparatus according to the present embodiment includes an arm unit (not shown) constituted of the arm 104. The arm 104 constituting the arm unit (not shown) supports the imaging device (for example, the first imaging device 120-1 and the second imaging device 120-2) constituting the imaging unit 150.

Moreover, for example, when the communicating with an external device through an external communication device having similar function and configuration to the communication unit 152, the medical observation apparatus according to the present embodiment does not need to include the communication unit 152.

Furthermore, when the medical observation system according to the present embodiment is configured to include a medical control apparatus (not shown), and when medical observation apparatus according to the present embodiment is controlled by the medical control apparatus, the medical observation apparatus according to the present embodiment does not need to include the control unit 154.

Equipped with, for example, a control unit having similar function and configuration to the control unit 154, the medical control apparatus (not shown) performs the processing related to the display control method according to the present embodiment described later, and controls operation of the respective components of the medical observation apparatus according to the present embodiment, such as the imaging unit 150. By communicating with the medical observation apparatus according to the present embodiment through a communication device included in the medical observation apparatus or through an external communication device connected thereto, the medical control apparatus (not shown) control operation of the respective components included in the medical observation apparatus according to the present embodiment.

Moreover, when the medical observation system according to the present embodiment is configured to include a medical control apparatus (not shown), and when the medical observation apparatus according to the present embodiment is controlled by the medical control apparatus, the medical observation apparatus according to the present embodiment can take a configuration not including part of the functions of the control unit 154.

Processing According to Display Control Method According to Present Embodiment

Next, the display control method according to the present embodiment is described. In the following, a case in which the medical observation apparatus 100 (more specifically, for example, the display control unit 158 included in the control unit 154 constituting the medical observation apparatus 100) performs the processing related to the display control method according to the present embodiment is described as an example. Note that the processing related to the display control method according to the present embodiment may be performed by the medical control apparatus (not shown) or the like in the medical observation system according to the present embodiment as described above.

[2-1] Overview of Processing According to Display Control Method According to Present Embodiment As described above, when the up-and-down direction of an imaging device, the direction toward which a medical staff faces, and the arrangement direction of a display device do not match with one another, the up-and-down direction in the display screen differs from the direction toward which the medical staff faces. As a result, intuitive operation by the medical staff can be interfered. When the intuitive operation can be interfered as described above, improvement of convenience for a person viewing the display screen on which a medical captured image is displayed cannot be expected.

As a method of aligning the directions when the up-and-down direction of the imaging device, the direction toward which the medical staff faces, and the arrangement direction of the display device do not match one another, for example, a method of rotating the display device, or a method of rotating an image to be displayed on the display device by image processing are considered.

As an example, a case in which an assistant is positioned at a position either on the right or left of operator, and performs a supporting work from a substantially 90° side direction from the operator is described as an example. In this example, the display device viewed by the assistant is rotated by 90°, or an image rotated by 90° by image processing is displayed on the display device, thereby enabling to "align the up-and-down direction of the imaging device, the direction toward which the medical staff faces, and the arrangement direction of the display device".

Figure 5:
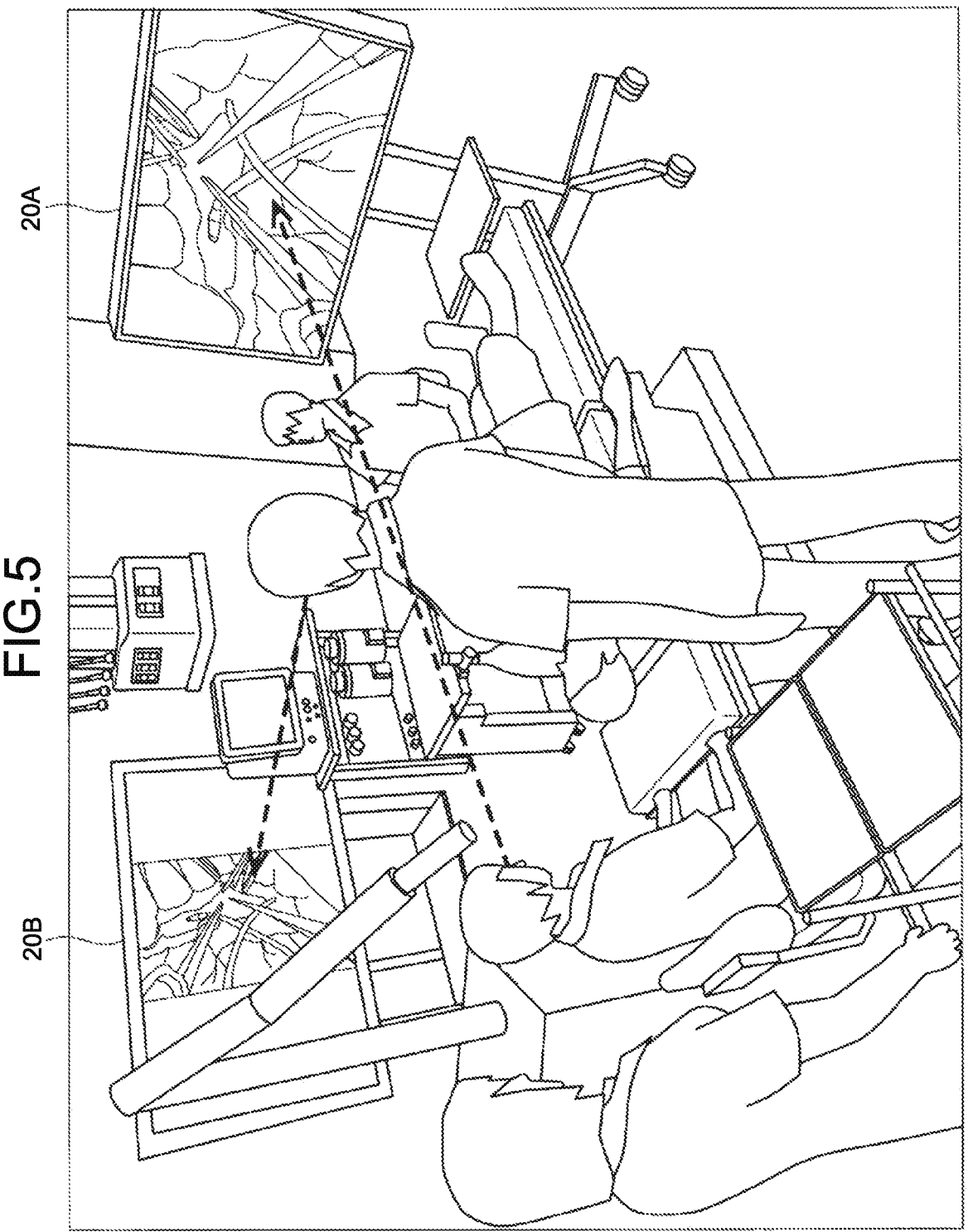
FIG. 5 is an explanatory diagram for explaining an example of a method of matching an up-and-down direction of the imaging device, a direction toward which a medical staff faces, and an arrangement direction of the display device.

FIG. 5 is an explanatory diagram for explaining an example of a method of aligning the up-and-down direction of the imaging device, the direction toward which a medical staff faces, and the arrangement direction of the display device. FIG. 5 illustrates an "example of aligning the up-and-down direction of the imaging device, the direction toward which the medical staff faces, and the arrangement direction of the display device by displaying an image rotated by 90° on the display device viewed by the assistant.

A display device 20A illustrated in FIG. 5 is a display device viewed by the operator. A display device 20B illustrated in FIG. 5 is a display device viewed by an assistant. The example illustrated in FIG. 5 is an example in which the assistant is positioned on the right of the operator, and the assistant performs a supporting work from a substantially 90° side direction from the operator.

Comparing with the display device 20A and the display device 20B, it is found that an image obtained by rotating a medical captured image displayed on a display screen of the display device 20A by 90° to the left is displayed on a display screen of the display device 20B.

Assuming that an image that is not rotated is displayed on the display screen of the display device 20B, the image displayed on the display screen of the display device 20B viewed by the assistant is to be an image that is rotated by 90° to the right relative to the assistant, and it causes a situation that movement of hands of the assistant and the orientation of the image do not match with each other. Therefore, when the image not rotated is displayed on the display screen of the display device 20B, it is difficult for the assistant to perform the supporting work while viewing the image, and convenience for the assistant can be reduced.

On the other hand, in the example illustrated in FIG. 5, an image obtained by rotating the medical captured image displayed on the display screen of the display device 20A by 90° to the left is displayed on the display screen of the display device 20B and, therefore, the movement of hands of the assistant and the orientation of the image match with each other. Therefore, the supporting work performed by the assistant while viewing the image is facilitated.

As in the example illustrated in FIG. 5, an aspect ratio of a display screen of a display device and an aspect ratio of a medical captured image captured by the imaging device generally have a width (horizontal direction) larger than a length (vertical direction). Therefore, either when the display device is rotated by 90°, or when an image just rotated by 90° is displayed on the display device, the image displayed on the display screen is to be a vertically-oriented image. When the vertically-oriented image is displayed on the display screen of the display device viewed by the assistant, a display range in a horizontal direction of the medical captured image to be displayed on the display screen is to be narrow for movement of hands of the assistant in a left and right direction. Furthermore, when an image just rotated by 90° is displayed on the display device, a black out range (range with no image) is generated on both left and right sides of the display screen, and there is a possibility that part of the medical captured image is not displayed due to restrictions in a display enabled range in the vertical direction of the display device.

Accordingly, even if the display device is rotated by 90°, or even if an image just rotated by 90° is displayed on the display device, convenience for the assistant (an example of a person viewing a display screen on which a medical captured image is displayed) is not necessarily improved.

The medical observation apparatus 100 displays the first medical captured-image and an image corresponding to a region that is set with respect to the second medical captured-image on display screens of the display devices 200 corresponding to the respective images.

As described later, the medical observation apparatus 100 sets a region with respect to the second medical captured-image so as to be suitable for the display device 200 that is a subject of display of the image corresponding to the region. That is, the medical observation apparatus 100 displays a part of the second medical captured-image according to the set region, not displaying a rotated medical captured-image as in the example illustrated in FIG. 5, and thereby aligns the up-and-down direction of the imaging device, the direction toward which the medical staff faces, and the arrangement direction of the display device.

As described above, an image corresponding to a region is a part of a partial image of the second medical captured-image that is imaged by the second imaging device 120-2 having more effective pixels than the first imaging device 120-1. Moreover, as illustrated in an example described later, when the display control method according to the present embodiment is used, the size of the image corresponding to the region can be adjusted to the size corresponding to the first medical captured-image. Therefore, when the image corresponding to the region is displayed on the display screen by the processing related to the display control method according to the present embodiment, a "disadvantage caused when an image just rotated by 90° is displayed on a display device" described above is not caused.

Therefore, the medical observation apparatus 100 that performs the processing related to the display control method according to the present embodiment can improve convenience for a person that views a display screen on which a medical captured image is displayed.

Hereinafter, an example of the processing related to the display control method according to the present embodiment is described more specifically. In the following, a case in which the first display device is the "display device 200A that is viewed by an operator", and the second display device is the "display device 200B that is viewed by an assistant" is described as an example. It is needless to say that the example of the first display device and the second display device are not limited to the example described above.

[2-2] First Example of Processing According to Display Control Method

[2-2-1] Example of Arrangement of Pixels in Each of First Imaging Device 120-1 and Second Imaging Device 120-2

First, an example of arrangement of pixels in each of the first imaging device 120-1 and the second imaging device 120-2 that is applicable to the display control method according to a first example is described.

Figure 6:
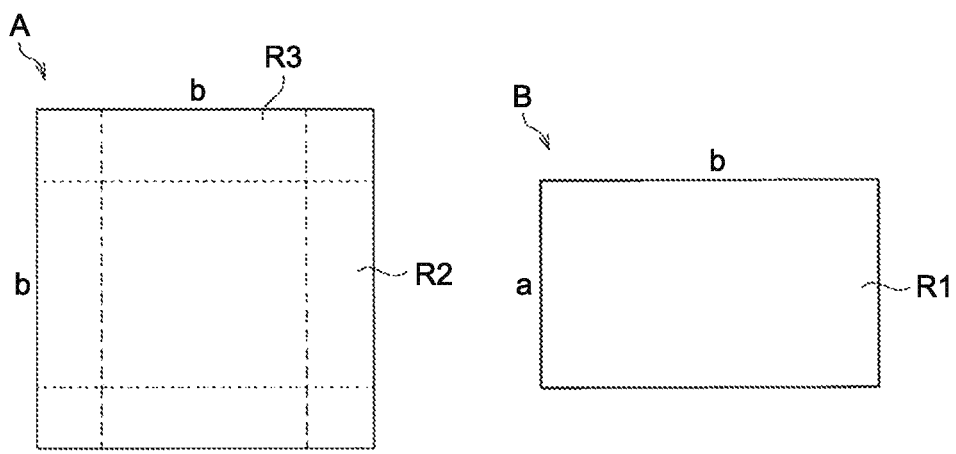
FIG. 6 is an explanatory diagram illustrating a first example of arrangement of effective pixels in the imaging device of the medical observation apparatus according to the present embodiment.

FIG. 6 is an explanatory diagram illustrating the first example of arrangement of effective pixels in the imaging device of the medical observation apparatus 100 according to the present embodiment. A in FIG. 6 illustrates an example of arrangement of effective pixels in multiple pixels in the second imaging device 120-2, and B in FIG. 6 illustrates an example of arrangement of effective pixels in multiple pixels in the first imaging device 120-1.

The pixels in the first imaging device 120-1 are arranged in a matrix. B in FIG. 6 illustrates an example in which the number of rows of the effective pixels is a (a is a positive integer), and the number of columns of the effective pixels is b (b is a positive integer satisfying b>a) in the first imaging device 120-1. That is, in B in FIG. 6, the number of rows and the number of columns of the effective pixels among the multiple pixels in the first imaging device 120-1 differ from each other.

The pixels in the second imaging device 120-2 are arranged in a matrix. A in FIG. 6 illustrates an example in which the number of rows and the number of columns of the effective pixels are a in the second imaging device 120-2. That is, in A in FIG. 6, the number of rows and the number of columns of the effective pixels in the second imaging device 120-2 are the same as a larger one out of the number of rows and the number of columns of the effective pixels in the first imaging device 120-1.

In each of the first imaging device 120-1 and the second imaging device 120-2, for example, by arranging the effective pixels as illustrated in FIG. 6, a region in the same size as the first medical captured-image can be set with respect to the second medical captured-image. That is, for example, with the arrangement of the effective pixels as illustrated in FIG. 6, the size of an image of a region set with respect to the second medical captured-image can be set to the same size as the first medical captured-image.

Note that the example of arrangement of the effective pixels in each of the first imaging device 120-1 and the second imaging device 120-2 to which the display control method according to the first example is applicable is not limited to the example illustrated in FIG. 6. For example, the number of rows and the number of columns of the effective pixels in the second imaging device 120-2 may be equal to or more than a larger one out of the number of rows and the number of columns of the effective pixels in the first imaging device 120-1. Moreover, at this time, the number of rows and the number of columns of the effective pixels in the second imaging device 120-2 may differ from each other.

[2-2-2] Example of Processing Related to Display Control Method According to First Example Next, processing related to the display control method according to the first example is described in a case in which the effective pixels are arranged as illustrated in FIG. 6 in each of the first imaging device 120-1 and the second imaging device 120-2, as an example.

The medical observation apparatus 100 sets one or both of a first region and a second region with respect to the second medical captured-image based on a predetermined selecting operation.

The first region according to the present embodiment corresponds to a region, an imaging area of an observation target of which is the same as the first medical captured-image. In the example illustrated in FIG. 6, a region R2 corresponds to the first region.

The second region according to the present embodiment corresponds to a region that is obtained by rotating the first region by 90° or by −90°. In the example illustrated in FIG. 6, a region R3 corresponds to the second region.

A magnitude of a rotation angle in the first region and the second region corresponds to an "angle formed by the orientation of the display screen of the first display device (for example, a perpendicular line direction of the display screen of the first display device) and the orientation of the display screen of the second display device (for example, a perpendicular line direction of the display screen of the second display device)". That is, the "case in which the second region is a region obtained by rotating the first region by 90° or by −90°" corresponds to a "case in which the orientation of the display screen of the second display device is perpendicular to the display screen of the first display device". Note that the "case in which the orientation of the display screen of the second display device is perpendicular to the display screen of the first display device" includes a case in which an angle formed by the orientation of the display screen of the second display device and the orientation of the display screen of the first display device is 90°, and a case in which the angle is 90+E2[°] (E2 is, for example, a "rational number corresponding to an allowable error that is set at a design stage or the like").

Examples of the predetermined selecting operation according to the first example include any operation, such as an "operation with respect to the operating device included in the medical observation apparatus 100", an "operation with respect to an external operating device outside the medical observation apparatus 100, such as a foot switch FS", an "operation by a gesture", and an "operation by voice".

When the selecting operation is an operation with respect to the operating device included in the medical observation apparatus 100, or an operation with respect to an external operating device, the medical observation apparatus 100 identifies the operation, for example, based on an operation signal according to the operation.

When the selecting operation is an operation by gesture, the medical observation apparatus 100 identifies the operation by gesture, for example, based on a "detection result of a gesture that is detected by arbitrary image processing with respect to a captured image in which a subject to operation detection is imaged". The image processing related to the detection may be performed by the medical observation apparatus 100, or may be performed in an external device outside the medical observation apparatus 100.

When the selecting operation is an operation by voice, the medical observation apparatus 100 identifies the operation by voice, for example, based on a "predetermined voice detection result that is detected by arbitrary signal processing with respect to voice acquired by a voice input device, such as a microphone". The voice input device may be a voice input device included in the medical observation apparatus 100, or may be an external voice input device outside the medical observation apparatus 100. The signal processing related to the selection operation with respect to voice may be performed by the medical observation apparatus 100, or may be performed by an external device outside the medical observation apparatus 100.

In the following, a case in which the selecting operation according to the first example is an operation with respect to the operating device included in the medical observation apparatus 100 is described as an example.

Figure 7:
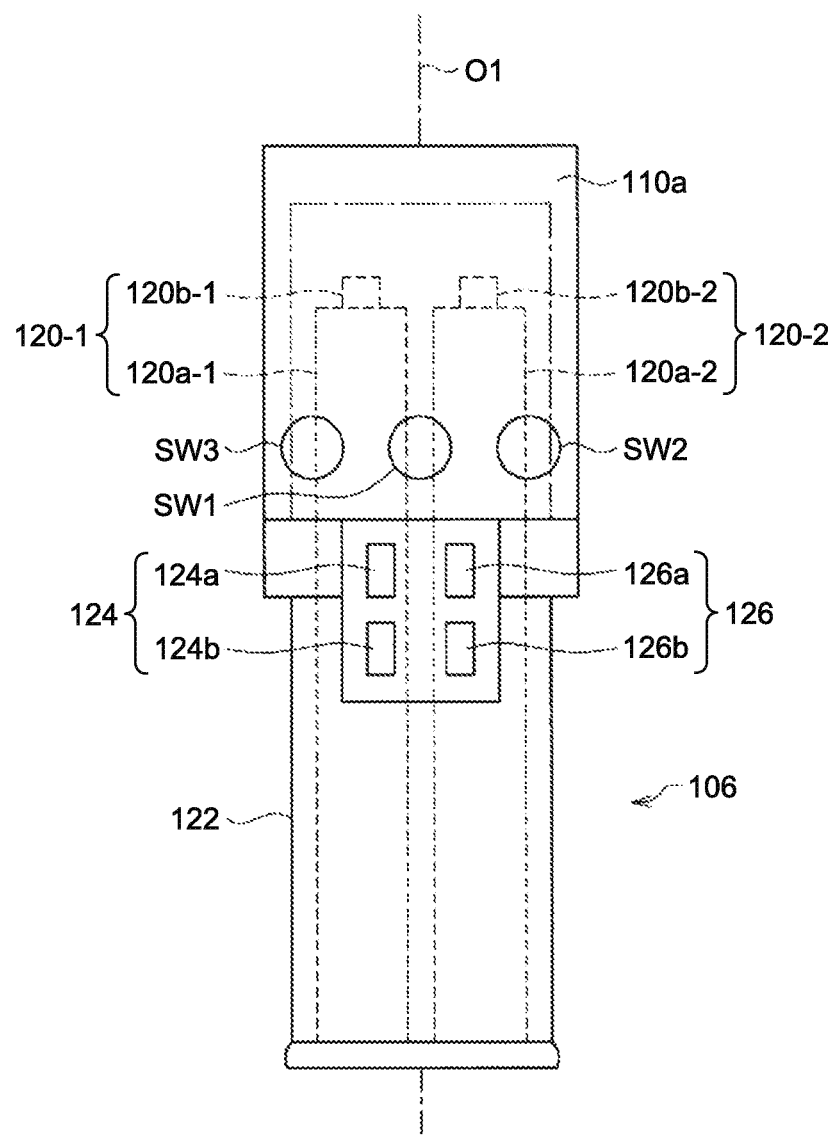
FIG. 7 is an explanatory diagram illustrating an example of an operating device with which a selecting operation is enabled in the medical observation apparatus according to the present embodiment.

FIG. 7 is an explanatory diagram illustrating an example of the operating device to perform a selecting operation included in the medical observation apparatus 100 according to the present embodiment. FIG. 7 illustrates an "example in which switches SW1, SW2, SW3 (an example of the operating device for the selecting operation) are provided in the imaging device unit 106 included in the medical observation apparatus 100 illustrated in FIG. 3". As the switches SW1, SW2, SW3, for example, a push down switch is considered, but the type of the switches SW1, SW2, SW3 is not particularly limited.

The example in which the operating device for the selecting operation is provided in the imaging device unit 106 is illustrated in FIG. 7, but the operating device for the selecting operation may be provided in another part other than the imaging device unit 106.

The switches SW1, SW2, SW3 correspond to switches to set, for example, the "orientation of the display screen of the second display device relative to the display screen of the first display device".

The switch SW1 is a switch to set the region R2 (an example of the first region. The same applies hereafter) in FIG. 6 with respect to the second medical captured-image. That is, a case in which the switch SW1 is subjected to the selecting operation corresponds to a case in which only the first region is set.

The switches SW2, SW3 are switches to set at least the region R3 (an example of the second region. The same applies hereafter) in FIG. 6 with respect to the second medical captured-image. When the switches SW2, SW3 are subject to the selecting operation, both of the region R2 and the region R3 may be set with respect to the second medical captured-image. That is, the case in which the switches SW2, SW3 are subjected to the selecting operation corresponds to the case in which one or both of the region R2 and the region R3 are set.

For example, when the switch SW1 is subjected to the selecting operation, the medical observation apparatus 100 sets only the region R2 with respect to the second medical captured-image. The medical observation apparatus 100 displays an image corresponding to the set region R2 on the display screen of the display device 200B. When the image corresponding to the region R2 is displayed only on the display screen of the display device 200B, the medical observation apparatus 100 displays the first medical captured-image on the display device 200A.

Moreover, when the switch SW1 is subjected to the selecting operation, the medical observation apparatus 100 may display the image corresponding to the set region R2 further on the display screen of the display device 200A. When the image corresponding to the region R2 is displayed on the display screen of the display device 200A, the medical observation apparatus 100 displays the firs medical captured-image and the image corresponding to the region R2 as a medical captured image for right eve and a medical captured image for left eye, respectively. In this case, the operator that views the display screen of the display device 200A can see a stereoscopic image of the observation target.

For example, when the switch SW2 is subjected to the selecting operation, the medical observation apparatus 100 sets only the region R3 with respect to the second medical captured-image. The medical observation apparatus 100 displays an image corresponding to the set region R3 on the display screen of the display device 200B. At this time, the medical observation apparatus 100 displays the image such that a left side of the image corresponding to the region R3 in FIG. 6 is displayed at an upper side of the display screen of the display device 200. In the medical observation apparatus 100, the display as described above may be implemented by performing rotation processing with respect to the image corresponding to the region R3, or the display as described above may be implemented by a control by the display control signal.

When the switch SW2 is subjected to the selecting operation, by displaying the image corresponding to the region R3 on the display screen of the display device 200B as described above, the image displayed on the display device is to be an appropriate image for the assistant that is positioned on the right side from the operator. Furthermore, when only the region R3 is set with respect to the second medical captured-image by subjecting the switch SW2 to the selecting operation, the medical observation apparatus 100 displays the first medical captured-image on the display device 200A.

Note that the region that is set when the switch SW2 is subjected to the selecting operation is not limited to the example described above. For example, when the switch SW2 is subjected to the selecting operation, the medical observation apparatus 100 may set the region R2 and the region R3 with respect to the second medical captured image. When the region R2 and the region R3 are set when the switch SW2 is subjected to the selecting operation, the medical observation apparatus 100 displays, for example, both the first medical captured-image and the image corresponding to the set region R2 on the display screen of the display device 200A. When the first medical captured-image and the image corresponding to the region R2 are displayed on the display screen of the display device 200A, the operator viewing the display screen of the display device 200A can see a stereoscopic image of the observation target.

For example, when the switch SW3 is subjected to the selecting operation, the medical observation apparatus 100 sets only the region R3 with respect to the second medical captured-image. The medical observation apparatus 100 displays the image corresponding to the region R3 on the display screen of the display device 200B. At this time, the medical observation apparatus 100 displays the image such that a right side of the image corresponding to the region R3 in FIG. 6 is displayed at an upper side of the display screen of the display device 200. In the medical observation apparatus 100, the display as described above may be implemented by performing rotation processing with respect to the image corresponding to the region R3, or the display as described above may be implemented by a control by the display control signal.

When the switch SW2 is subjected to the selecting operation, by displaying the image corresponding to the region R3 on the display screen of the display device 200B as described above, the image displayed on the display device is to be an appropriate image for the assistant that is positioned on the left side from the operator. Furthermore, when only the region R3 is set with respect to the second medical captured-image by subjecting the switch SW2 to the selecting operation, the medical observation apparatus 100 displays the first medical captured-image on the display device 200A.

Note that the region that is set when the switch SW3 is subjected to the selecting operation is not limited to the example described above. For example, when the switch SW3 is subjected to the selecting operation, the medical observation apparatus 100 may set the region R2 and the region R3 with respect to the second medical captured-image. When the region R2 and the region R3 are set when the switch SW3 is subjected to the selecting operation, the medical observation apparatus 100 displays, for example, both the first medical captured-image and the image corresponding to the set region R2 on the display screen of the display device 200A. When the first medical captured-image and the image corresponding to the region R2 are displayed on the display screen of the display device 200A, the operator viewing the display screen of the display device 200A can see a stereoscopic image of the observation target.

Figure 9:
FIG. 9 is an explanatory diagram for explaining an example of an image displayed on the display screen of the display device by the first example of processing related to the display control method according to the present embodiment.

FIG. 8 and FIG. 9 are explanatory diagrams for explaining an example of an image displayed on a display screens of the display device 200A, 200B by the first example of processing related to the display control method according to the present embodiment.

A in FIG. 8 illustrates an example of the first medical captured-image that is displayed on the display screen of the display device 200A viewed by the operator. When the switch SW1 is subjected to the selecting operation, an image illustrated in A in FIG. 8 is to be displayed on the display screen of the display device 200B. As described above, when the switch SW1 is subjected to the selecting operation, the first medical captured-image and the image corresponding to the region R2 may be displayed as a stereoscopic image on the display screen of the display device 200B.

B in FIG. 8 illustrates an example of an image corresponding to the region R3 that is displayed on the display screen of the display device 200B viewed by the assistant when the switch SW2 is subjected to the selecting operation. Moreover, C in FIG. 8 illustrates an example of an image corresponding to the region R3 that is displayed on the display screen of the display device 200B viewed by the assistant when the switch SW3 is subjected to the selecting operation. As illustrated in B in FIG. 8 and in FIG. 9, when the switch SW2 is subjected to the selecting operation, an image appropriate for a position of the assistant can be displayed on the display screen of the display device 200B even when the assistant is positioned in a substantially 90° side direction to the right from the operator. Similarly, as illustrated in C in FIG. 8, when the switch SW3 is subjected to the selecting operation, an image appropriate for a position of the assistant can be displayed on the display screen of the display device 200B even when the assistant is positioned in a substantially 90° side direction to the left from the operator and the display device 200B is positioned in front of the assistant.

[2-2-3] Example of Effect Produced by Processing Related to Display Control Method According to First Example By performing the processing related to the display control method according to the first example, for example, an effect described below is produced. It is needless to say that the effect produced by using the display control method according to first example is not limited to the example described below.

It is possible to adjust an image displayed on the display screen of the display device 200B to be in an orientation of the image according to a position of an assistant by the predetermined selecting operation, such as the selecting operation with respect to a switch arranged in the imaging device unit 106, or the like.

[2-3] Second Example of Processing Related to Display Control Method

[2-3-1] Example of Arrangement of Pixels in Each of First Imaging Device 120-1 and Second Imaging Device 120-2

First, an example of arrangement of multiple pixels in each of the first imaging device 120-1 and the second imaging device 120-2 that is applicable to the display control method according to the second example is described.

Figure 10:
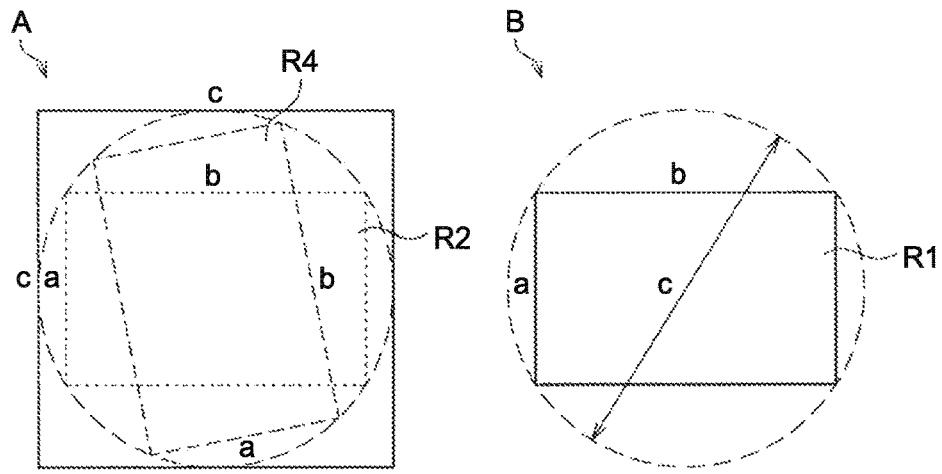
FIG. 10 is an explanatory diagram illustrating a second example of arrangement of the effective pixels in the imaging device of the medical observation apparatus according to the present embodiment.

FIG. 10 is an explanatory diagram illustrating a second example of arrangement of the effective pixels in the imaging device of the medical observation apparatus 100 according to the present embodiment. A in FIG. 10 illustrates another example of arrangement of the effective pixels in the second imaging device 120-2, and B in FIG. 10 illustrates another example of arrangement of the effective pixels in the first imaging device 120-1.

The pixels in the first imaging device 120-1 are arranged in matrix. B in FIG. 10 illustrates an example in which the number of rows of the effective pixels is a, and the number of columns of the effective pixels is b in the first imaging device 120-1 similarly to the first imaging device 120-1 illustrated in B in FIG. 6. That is, in B in FIG. 10, the number of rows and the number of columns of the effective pixels in the first imaging device 120-1 differ from each other.

The pixels in the second imaging device 120-2 are arranged in matrix. A in FIG. 10 illustrates an example in which the number of rows and the number of columns of the effective pixels is c (c is a positive integer) in the second imaging device 120-2. AS illustrated in B in FIG. 10, c is a "value of a diameter of a circumcircle of a rectangle in which the number of rows and the number of columns of the effective pixels in the first imaging device 120-1 constitute respective sides". When the value of the diameter of the circumcircle is not a positive integer, a positive integer larger than the diameter of the circumcircle is considered as the value of c. Moreover, when the value of the diameter of the circumcircle is a positive integer also, the value of c may be a positive integer larger than the diameter of the circumcircle. That is, as the number of rows and the number of columns of the effective pixels in the second imaging device 120-2, a value equal to or larger than a diameter of a circumcircle of a rectangle in which the number of rows and the number of columns of the effective pixels in the first imaging device 120-1 constitute respective sides is considered.

By arranging the effective pixels, for example, as illustrated in FIG. 10 in each of the first imaging device 120-1 and the second imaging device 120-2, a region in the same as the first medical captured-image can be set with respect to the second medical captured-image. That is, for example, by the arrangement of pixels as illustrated in FIG. 10, it is possible to make the size of the image of the region set with respect to the second medical captured-image same as the first medical captured-image.

Note that the example of arrangement of the effective pixels in each of the first imaging device 120-1 and the second imaging device 120-2 that is applicable to the display control method according to the second example is not limited to the example illustrated in FIG. 10. For example, the number of rows and the number of columns of the effective pixels in the second imaging device 120-2 may be different from each other.

[2-3-2] Example of Processing According to Display Control Method According to Second Example Next, the processing related to the display control method according to the second example is described with a case in which the effective pixels are arranged as illustrated in FIG. 10 in each of the first imaging device 120-1 and the second imaging device 120-2 as an example.

The medical observation apparatus 100 sets one or both of the first region and the third region with respect to the second medical captured-image based on a predetermined selecting operation.

In the example illustrated in FIG. 10, the region R2 corresponds to the first region.

The third region according to the present embodiment is a region obtained by rotating the first region based on a predetermined selecting operation. In the example illustrated in FIG. 10, a region R4 corresponds to the third region.

Examples of the predetermined selecting operation according to the second example include any operation, such as an "operation with respect to the operating device included in the medical observation apparatus 100", an "operation with respect to an external operating device outside the medical observation apparatus 100, such as the foot switch FS", an "operation by a gesture", and an "operation by voice", similarly to the predetermined selecting operation according to the first example.

In the following, a case in which the selecting operation according to the second example is an operation with respect to the operating device included in the medical observation apparatus 100 is described as an example.

Figure 11:
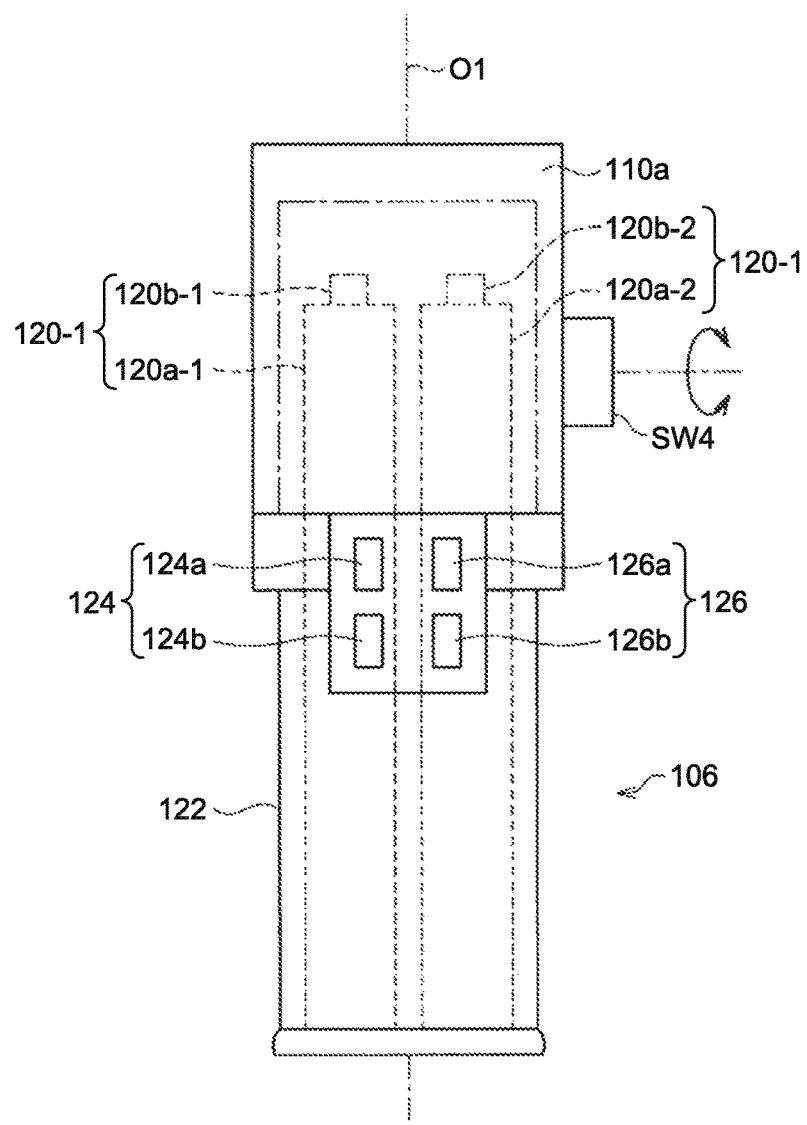
FIG. 11 is an explanatory diagram illustrating another example of the operating device to perform a selecting operation in the medical observation apparatus according to the present embodiment.

FIG. 11 is an explanatory diagram illustrating another example of the operating device to perform a selecting operation in the medical observation apparatus according 100 to the present embodiment. FIG. 11 illustrates an "example in which a switch SW4 (an example of the operating device for the selecting operation) to perform the selecting operation is arranged in the imaging device unit 106 included in the medical observation apparatus 100 illustrated in FIG. 3". As the switch SW4, for example, a dial switch is considered, but the type of the switch SW4 is not particularly limited.

The example in which the operating device for the selecting operation is arranged in the imaging device unit 106 is illustrated in FIG. 11, but the operating device for the selecting operation may be arranged in another part other than the imaging device unit 106.

The switch SW4 corresponds to a switch to set the orientation of the second display device relative to the orientation of the first display device more precisely than the case of setting it by the selecting operation with respect to the switches SW1, SW2, SW3 illustrated in FIG. 7.

The orientation of the display screen of the second display device relative to the orientation of the display screen of the first display device can be indicated by an angle formed by the orientation of the display screen of the first display device and the orientation of the display screen of the second display device. For example, the first example described above is an example in which the above angle is set to 0°, 90°, or −90° by the selecting operation with respect to the switches SW1, SW2, SW3. By increasing selectable angles with the switch SW4, the orientation of the display screen of the second display device relative to the orientation of the display screen of the first display device can be set more linearly than in the first example.

For example, when the angle formed between the orientation of the display screen of the first display device and the orientation of the display screen of the second display device is set to 0° by the selecting operation with respect to the switch SW4, the medical observation apparatus 100 sets only the region R2 with respect to the second medical captured-image. The above case corresponds to the case in which the switch SW illustrated in FIG. 7 is subjected to the selecting operation. That is, the above case corresponds to the case in which only the first region is set.

The medical observation apparatus 100 displays an image corresponding to the set region R2 on the display screen of the display device 200B. When the image corresponding to the region R2 is displayed on the display screen of the display device 200B, the medical observation apparatus 100 displays the first medical captured-image on the display device 200A.

The medical observation apparatus 100 may further display the image corresponding to the set region R2 on the display screen of the display device 200A. When the image corresponding to the region R2 is displayed on the display screen of the display device 200A, the medical observation apparatus 100 displays the first medical captured-image and the image corresponding to the region R2 as a medical captured image for right eye and a medical captured image for left eye, respectively.

Moreover, for example, when the angle formed between the orientation of the display screen of the first display device and the orientation of the display screen of the second display device is set to an angle other than 0° by the selecting operation with respect to the switch SW4, the medical observation apparatus 100 sets only the region R4 according to the set angle with respect to the second medical captured-image. The medical observation apparatus 100 displays an image corresponding to the set region R4 on the display screen of the display device 200B. When only the region R4 is set with respect to the second medical captured-image, the medical observation apparatus 100 displays the first medical captured-image on the display device 200A.

Note that the region set when the angle formed between the orientation of the display screen of the first display device and the orientation of the display screen of the second display device is set to an angle other than 0° by the selecting operation with respect to the switch SW4 is not limited to the example described above. For example, in the above case, the medical observation apparatus 100 may set the region R2 and the region R4 with respect to the second medical captured-image. When the region R2 and the region R4 are set when the switch SW4 is subjected to the selecting operation, the medical observation apparatus 100 displays both of the first medical captured-image and the image corresponding to the set region R2 on the display screen of the first display device 200A. When the first medical captured-image and the image corresponding to the region R2 are displayed on the display screen of the first display device 200A, the operator viewing the first display device 200A can see a stereoscopic image of the observation target.

[2-3-3] Example of Effect Produced by Processing Related to Display Control Method According to Second Example By performing the processing related to the display control method according to the second example, for example, an effect described below is produce. It is needless to say that the effect produced by using the display control method according to second example is not limited to the example described below.

Even when a position of an assistant is shifted from a 90 degree position to the left or right from an operator, it is possible to set a region with respect to second medical captured-image so as to match with a positional relations between the operator and the assistant. By setting a region respect to the second medical captured-image as described above, it is possible to display an image in which an up-and-down and a left-and right directions match with those at the position of the assistant on the display screen of the display device 200B and, therefore, hand-eye coordination can be obtained.

[2-4] Third Example of Processing Related to Display Control Method

In the processing related to the display control method according to the first example and the processing related to the display control method according to the second example, an example of the processing in which a region is set with respect to the second medical captured-image based on the predetermined selection operation has been described. However, processing related to the display control method according to the present embodiment is not limited to the processing in which a region is set with respect to the second medical captured-image based on a selecting operation.

For example, the medical observation apparatus 100 can set a region with respect to the second medical captured-image automatically, not based on a selecting operation.

[2-4-1] Example of Arrangement of Pixels in Each of First Imaging Device 120-1 and Second Imaging Device 120-2

First, an example of arrangement of multiple pixels in each of the first imaging device 120-1 and the second imaging device 120-2 that is applicable to a display control method according to a third example is described. As the arrangement of pixels that is applicable to a display control method according to the third example, an arrangement similar to the arrangement of the pixels according to the display control method according to the second example described above, such as the arrangement illustrated in FIG. 10, is considered.

The medical observation apparatus 100 sets one or both of the first region and a fourth region with respect to the second medical captured-image based on a result of detection of relative position between the imaging unit 150 and a predetermined observer.

As described above, the region R2 corresponds to the first region in the example illustrated in FIG. 10.

The fourth region according to the present embodiment is a region obtained by rotating the first region based on the result of detection of the relative position between the imaging unit 150 and the predetermined observer. In the example illustrated in FIG. 10, the region R4 corresponds to the fourth region.

The relative position between the imaging unit 150 and the observer is detected by identifying, for example, a "relative angle between the imaging device unit 106 serving as the imaging unit 150 and the head of the predetermined observer" (hereinafter, simply referred to as "relative angle" in some cases). As the predetermined observer, a person that views the second display device, such as an assistant, is considered.

The relative angle is identified by identifying the orientation of the imaging device unit 106 (for example, the up-and-down direction of the imaging device) and the orientation of the predetermined observer (for example, a direction toward which the face of the observer faces) by using light of an arbitrary wavelength, such as infrared light. When the light used to identify the relative angle is light having a wavelength other than that of visible light, such as infrared light, the light is difficult to be visually identified by a medical staff at a medical site at which the medical observation system 1000 is used. therefore, in the above case, there is an "advantage that light used to identify the relative angle does not interfere medical treatment performed by the medical staff". In the following, a case in which light used to identify the relative angle is infrared ray is described as an example, but the light is not limited to infrared light.

Figure 12:
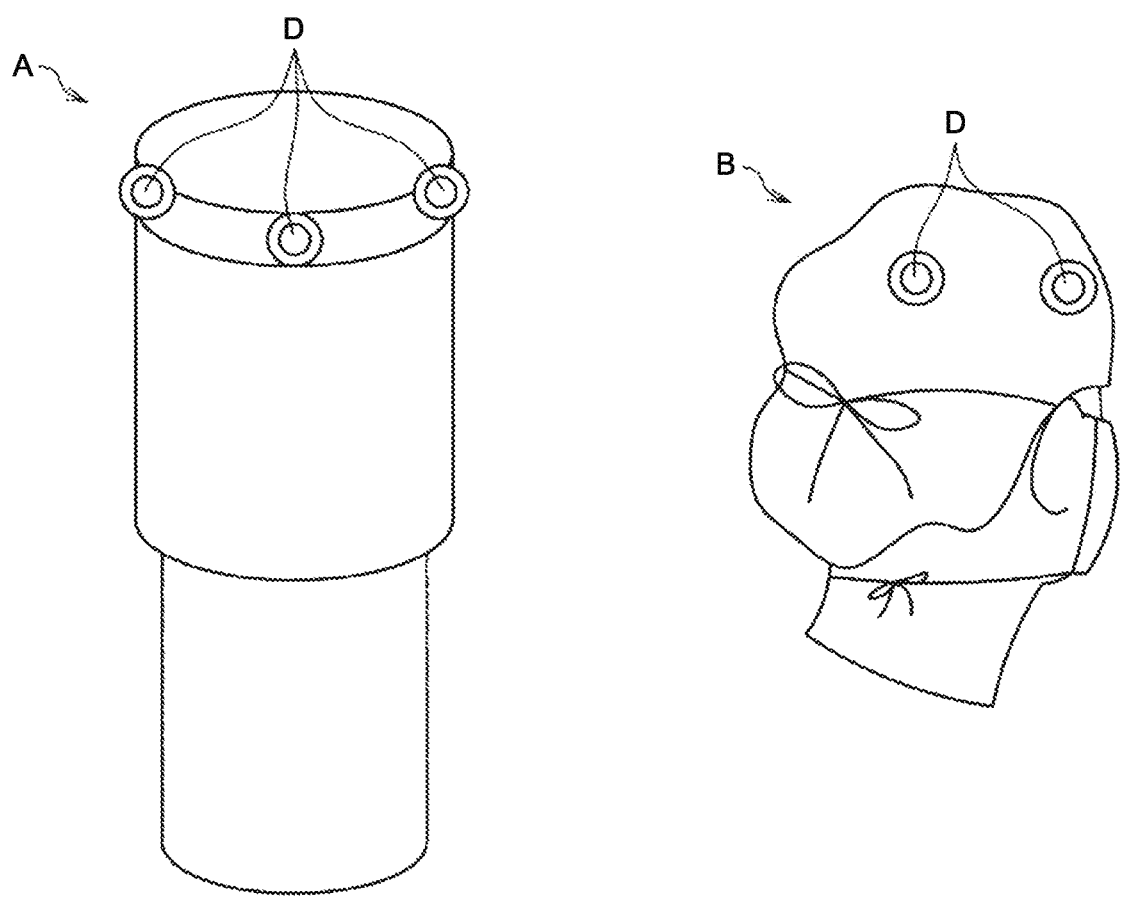
FIG. 12 is an explanatory diagram for explaining a third example of processing related to the display control method according to the present embodiment.

FIG. 12 is an explanatory diagram for explaining a third example of the processing related to the display control method according to the present embodiment. A in FIG. 12 illustrates an example in which multiple light emitting diodes D are arranged in the imaging device unit 106 serving as the imaging unit 150. Moreover, B in FIG. 12 illustrates an example in which the multiple light emitting diodes D are arranged at the head of the predetermined observer. To the light emitting diodes D, power is supplied from a power source, such as a battery, and the light emitting diodes D emit light of a predetermined wavelength, such as infrared light. The control of light emission of each of the light emitting diodes D may be performed by the medical observation apparatus 100, or may be performed by an external device outside the medical observation apparatus 100.

The respective light emitting diodes D arranged on the imaging device unit 106 emit light in different emission modes from one another. Being different in the light emission modes from one another is implemented by "emitting light in emission patterns different from one another by the respective light emitting diodes D", by "emitting light in light intensities different from one another by the respective light emitting diodes D", or by "varying combinations of the emission pattern and the light intensity from one another in the respective t emitting diodes D".

Furthermore, the respective light emitting diodes D arranged on the head of the predetermined observer differ in the light emission modes from one another, similarly to the light emitting diodes D arranged on the imaging device unit 106.

The light emission from the light emitting diodes D arranged on the imaging device unit 106 and the light emission from the light emitting diode D arranged on the head of the predetermined observer are detected by imaging by the imaging device arranged in a medical site in which the medical observation apparatus 100 is used.

Because the respective light emitting diodes D arranged on the imaging device unit 106 emit light in different modes from one another, if the light emission modes are known, it is possible to identify the orientation of the imaging device unit 106 by identifying the light emission modes of the light emitting diodes D. Similarly, because the respective light emitting diodes D arranged on the head of the predetermined observer emit light in different modes from one another, it is possible to identify the orientation of the predetermined observer by identifying the light emission modes of the light emitting diodes D. Furthermore, when the orientation of the imaging device unit 106 and the orientation of the predetermined observer are identified, the relative angle can be acquired.

The processing of identifying the orientation of the imaging device unit 106, the processing of identifying the orientation of the predetermined observer, and the processing of acquiring the relative angle may be performed by the medical observation apparatus 100, or may be performed by an external device outside the medical observation apparatus 100. Furthermore, the processing of identifying the orientation of the imaging device unit 106, the processing of identifying the orientation of the predetermined observer, and the processing of acquiring the relative angle may be performed in cooperation by multiple devices. It is needless to say that the example of processing of identifying the relative angle is not limited to the example described above.

Note that the method of detecting the relative position between the imaging device unit 106 and the predetermined observer is not limited to the processing of detecting the relative angle as described above, and arbitrary processing enabling to detect the relative position between the imaging device unit 106 and the predetermined observer may be applied.

When the relative position between the imaging unit 150 and the predetermined observer is detected, the medical observation apparatus 100 sets a region corresponding to the relative angle corresponding to the relative position with respect to the second medical captured-image. In the following, the relative position between the imaging unit 150 and the predetermined observer can be referred to as "relative position" simply.

The medical observation apparatus 100 sets a region corresponding to the relative position with respect to the second medical captured-image each time the relative position changes. The medical observation apparatus 100 may set a region corresponding to the relative position with respect to the second medical captured-image, regardless of whether the relative position changes, but each time the relative position is detected. When a region corresponding to the relative position is set with respect to the second medical captured-image each time the relative position changes, it is highly possible that the frequency of setting a region becomes low compared with the case of setting a region corresponding to the relative position each time the relative position is detected. Therefore, when a region corresponding to the relative position is set each time the relative position changes, it is possible to reduce power consumption in the medical observation apparatus 100 compared with the case in which a region corresponding to the relative position is set each time the relative position is detected.

For example, when the relative angle corresponding to the relative position is 0°, the medical observation apparatus 100 sets only the region R2 with respect to the second medical captured-image. The above case corresponds to the case in which only the first region is set.

The medical observation apparatus 100 displays an image corresponding to the set region R2 only on the display screen of the display device 200B. When the image corresponding to the set region R2 is displayed only on the display screen of the display device 200B, the medical observation apparatus 100 displays the first medical captured-image on the display device 200A.

Note that the medical observation apparatus 100 may display the image corresponding to the set region R2 further on the display screen of the display device 200A. When displaying the image corresponding to the region R2 on the display screen of the display device 200A, the medical observation apparatus 100 displays the first medical captured-image and the image corresponding to the region R2 as a medical captured image for right eye and a medical captured image for left eye, respectively.

Moreover, for example, when the relative angle corresponding to the relative position is an angle other than 0°, the medical observation apparatus 100 sets only the region R4 corresponding to the relative angle with respect to the second medical captured-image. The medical observation apparatus 100 displays an image corresponding to the set region R4 on the display screen of the display device 200B. When only the region R4 is set with respect to the second medical captured-image, the medical observation apparatus 100 displays the first medical captured-image on the display device 200A.

The region set when the relative angle corresponding to the relative position is an angle other than 0° is not limited to the example described above. For example, in the above case, the medical observation apparatus 100 may set the region R2 and the region R4 with respect to the second medical captured-image. When the region R2 and the region R4 are set with respect to the second medical captured-image based on the relative angle corresponding to the relative position, the medical observation apparatus 100 displays, for example, the first medical captured-image and the image corresponding to the set region R2 on the display screen of the display device 200A. When the first medical captured-image and the image corresponding to the region R2 are displayed on the display screen of the display device 200A, the operator viewing the display screen of the display device 200A can see a stereoscopic image of the observation target.

[2-4-3] Example of Effect Produced by Processing Related to Display Control Method According to Third Example By performing the processing related to the display control method according to the third example, for example, an effect described below is produced. It is needless to say that the effect produced by using the display control method according to the third example is not limited to the example described below.

By automatically detecting a relative position between the imaging device unit 106 and an assistant, a region is set with respect to the second medical captured-image so as to correspond to the relative position. When the up-and-down direction of the imaging device unit 106 matches with the orientation of the operator, a region is set with respect to the second medical captured-image so as to correspond to the positional relation between the operator and the assistant. By setting the region with respect to the second medical captured-image as described above, it is possible to display an image, the up-and-down direction of which matches with that at the position of the assistant on the display screen of the display device 200B and, therefore, the hand-eye coordination is obtained.

By automatically setting a region with respect to the second medical captured-image, it becomes unnecessary for a medical staff, such as the assistant and the operator, to perform an operation to set a region. Therefore, no trouble is given to the medical staffs about setting a region, and convenience for the medical staffs can be further improved.

[2-5] Fourth Example of Processing Related to Display Control Method.

Processing enabling to set a region with respect to the second medical captured-image is not limited to the processing related to the display control method according to the third example described above.

For example, the medical observation apparatus 100 may re-set a region corresponding to a relative position selectively according to a degree of change in the relative position between the imaging unit 150 and the predetermined observer in the processing related to the display control method according to the third example described above.

Specifically, the medical observation apparatus 100 sets a region corresponding to a relative position with respect to the second medical captured-image when the degree of change in the relative position becomes equal to or larger than a threshold that has been set (or when the degree of change in the relative position becomes larger than the threshold. The same applies hereafter). The threshold may be a fixed value set in advance to, for example, 5°, or the like, or may be a variable value that can be changed based on an operation by a user of the medical observation apparatus 100.

Furthermore, the medical observation apparatus 100 displays an image of a set region on the display screen of the corresponding display device 200, similarly to the processing related to the display control method according to the third example described above. That is, the processing related to the display control method according to a fourth example differs from the processing related to the display control method according to the third example described above, in a point that a region corresponding to the relative position is re-set selectively according to a degree of change in the relative position.

Because the processing related to the display control method according to the fourth example is processing similar to the processing related to the display control method according to the third example basically, a similar effect to the effect produced by the processing related to the display control method according to the third example is produced.

Moreover, when the processing related to the display control method according to the fourth example is performed, for example, when the change in the relative position becomes the predetermined threshold or larger, a region corresponding to the relative position is re-set with respect to the second medical captured-image. Therefore, when the processing related to the display control method according to the fourth example is performed, it is highly possible that the frequency of setting a region corresponding to the relative position is low compared with the case in which the processing related to the display control method according to the third example is performed. That is, when the processing related to the display control method according to the fourth example is performed, a change in an image of a region resetting of the region is small compared with the case in which the processing related to the display control method according to the third example is performed. Therefore, it is possible to avoid images to be displayed on the display screen from being change frequently. Accordingly, when the processing related to the display control method according to the fourth example is performed, it is possible to reduce discomfort felt by a person that views the display screen compared with the case in which the processing related to the display control method according to the third example is performed, and convenience for a person that views the display screen can be further improved.

[2-6] Fifth Example of Processing Related to Display Control Method

Processing enabling to set a region with respect to the second medical captured-image automatically is not limited to the processing related to the display control method according to the third example and the processing related to the display control method according to the fourth example described above.

For example, the medical observation apparatus 100 can set a region with respect to the second medical captured-image automatically, similarly to the processing related to the display control method according to the third example and the processing related and the display control method according to the fourth example described above, for example, when predetermined conditions described in (a) and (b) below are satisfied. Moreover, the medical observation apparatus 100 displays an image of a set region on the display screen of the corresponding display device 200, similarly to the processing related to the display control method according to the third example and the processing related to the display control method according to the fourth example described above.

(a) First Example of Setting Region Based on Predetermined Conditions

The medical observation apparatus 100 starts setting of a region corresponding to the relative position with respect to the second medical captured-image when one or both of the position and the orientation of the imaging unit 150 change.

That one or both of the position and the orientation of the imaging unit 150 change corresponds to that one or both of the position and the orientation of the imaging device unit 106 serving as the imaging unit 150 change. The change of the position and the orientation of the imaging device unit 106 is, for example, detected by an angle sensor (not shown) that is provided in each of the joints 110a, 110b, 110c, 110d, 110e, 110f described above. Note that the change of the position and the orientation of the imaging device unit 106 can be detected by any method enabling to detect each change.

Furthermore, the medical observation apparatus 100 does not change a set region corresponding to the relative position when the position and the orientation of the imaging unit 150 do not change for a predetermined period after the setting of a region corresponding to the relative position is started. The predetermined period may be a fixed period that has been set in advance, or may be a period variable based on an operation by a user of the medical observation apparatus 100.

When the predetermined conditions according to the first example are satisfied, and when a region is set with respect to the second medical captured-image, for example, when the operator moves the imaging device unit 106, automatic setting of a region with respect to the second medical captured-image is performed. Moreover, in the above case, a region set with respect to the second medical captured-image is fixed after a predetermined period passes after movement of the imaging device unit 106 by the operator is completed.

(b) Second Example of Setting Region Based on Predetermined Conditions

As described referring to FIG. 1, the imaging device unit 106 serving as the imaging unit 150 is supported by the arm 104. Moreover, as described above, the operation mode of the arm 104 includes, for example, the fixed mode (the second operation mode) and the free mode (the first operation mode).

The medical observation apparatus 100 sets a region corresponding to the relative position with respect to the second medical captured-image when the operation mode of the arm 104 is the free mode in which the position and the orientation of the imaging unit 150 are not fixed.

Furthermore, the medical observation apparatus 100 does not change a set region corresponding to the relative position when the operation mode of the arm 104 is the fixed mode in which the position and the orientation of the imaging unit 150 are fixed.

When the predetermined conditions according to the second example are satisfied, and when a region is set with respect to the second medical captured-image, automatic setting of a region with respect to the second medical captured-image is performed "upon the medical observation apparatus 100 turning into a state enabled to move the imaging device unit 106". Moreover, in the above case, a region set with respect to the second medical captured-image is fixed when "the medical observation apparatus 100 turns into a state disabled to move the imaging device unit 106.

[3] Example of Effect Produced by Using Display Control Method According to Present Embodiment (Effect Produced by Using Medical Observation System According to Present Embodiment)

By using the display control method according to the present embodiment, for example, an effect described below is produced. It is needless to say that the effect produced by using the display control method according to the present embodiment is not limited to the example described below.

It is possible to display an image in which the up-and-down and left-and-right directions match with those at a position of an assistant on the display screen of the display device 200B regardless of the position of the assistant being on left or right relative to an operator. Therefore, movement of hands of the assistant and movement of hands of himself/ herself in the image match each with each other, and the assistant can support the operator more reliably.

Because the medical observation apparatus to which the display control method according to the present embodiment is applied is implemented by a simple configuration of varying the sizes of the image sensor included in the first imaging device 120-1 and the image sensor included in the second imaging sensor 120-2, it is possible to avoid increase in size of an electronic-imaging microscope. Moreover, being able to avoid increase in size of the electronic-imaging microscope, decrease of treatment space for an operator can be suppressed, and as a result, reduction in operation work efficiency of the operator can be prevented.

Program According to Present Embodiment

By a program to cause a computer system to function as the medical observation apparatus according to the present embodiment (for example, program enabling to perform the processing related to the display control method according to the present embodiment) being executed by a processor in the computer system, convenience for a person that views a display screen on which a medical captured image is displayed can be improved. As the computer system according to the present embodiment, a single unit of computer or multiple units of computers are considered. A series of processing related to the display control method according to the present embodiment is performed by the computer system according to the present embodiment.

Furthermore, by a program that causes a computer system to function as the medical observation apparatus according to the present embodiment (or the medical display control apparatus according to the present embodiment) being executed by a processor or the like in the computer system, the effect that is produced by the display implemented by the display control method according to the present embodiment can be produced.

As above, the exemplary embodiments of the present disclosure have been described in detail with reference to the accompanying drawings, but a technical scope of the present disclosure is not limited to the examples. It is obvious that those having general knowledge in the technical field of the present disclosure can think of various alterations or modifications within a range of technical thought described in claims, and is understood that these, of course, are included in the technical scope of the present disclosure also.

For example, in the above, it is described that a program (computer program) to cause a computer system to function as the medical observation apparatus according to the present embodiment (or the medical display control apparatus according to the present embodiment) is provided, but the present embodiment can also provide a recording medium that stores the program along therewith.

The configuration described above indicates an example of the present embodiment and, of course, is included in the technical scope of the present disclosure.

Moreover, the effects described in the present application are only for explanation and exemplification, and are not limited. That is, the technique according to the present disclosure can produce other effects that are apparent from description of the present application to those skilled in the art instead of the above effects.

Note that following configurations are also included in the technical scope of the present disclosure.

(1)

A medical observation apparatus including
a camera that includes
a first imager including multiple pixels, and configured to image a first medical captured-image in which an observation target is imaged, and
a second imager having multiple pixels, and configured to image a second medical captured-image in which the observation target is imaged, the second imager including more effective pixels than the first imager; and
a display controller configured to cause displays to display the first medical captured-image and an image that corresponds to a region set with respect to the second medical captured-image on a display screen of the respective one of the displays corresponding thereto, wherein
one of the first medical captured-image and the second medical captured-image is a medical captured image for right eye, and
another one of the first medical captured-image and the second medical captured-image is a medical captured image for left eye.

(2)

The medical observation apparatus described in (1), wherein the display controller is configured to
set one of or both of a first region having a same imaging range for the observation target as the first medical captured-image, and a region that is obtained by rotating the first region with respect to the second medical captured-image,
display the first medical captured-image on a first display, or displays the first medical captured-image and an image that corresponds to the first region set with respect to the second medical captured-image on the first display as a stereoscopic image, and
display the image that corresponds to the first region set with respect to the second medical captured-image, or an image that corresponds to the region obtained by rotating the first region set with respect to the second medical captured-image on a display screen of a second display that is different from the first display.

(3)

The medical observation apparatus described in (2), wherein
the display controller is configured to
display the first medical captured-image and the image that corresponds to the first region set with respect to the second medical captured-image on the first display, and
display the image that corresponds to the region obtained by rotating the first region set with respect to the second medical captured-image on the second display, and
the image displayed on the second display is an image obtained by rotating the image corresponding to the region that is obtained by rotating the first region set with respect to the second medical captured-image so as to be suitable for the second display.

(4)

The medical observation apparatus described in any one of (1) to (3), wherein
the pixels in the first imager are arranged in a matrix, and the number of rows and the number of columns of effective pixels among the pixels are different from each other, and
the pixels in the second imager are arranged in a matrix, and the number of rows and the number of columns of effective pixels among the pixels are same as a larger one out of the number of rows and the number of columns of the effective pixels in the first imager.

(5)

The medical observation apparatus described in (2), wherein
the pixels in the first imager are arranged in a matrix, and the number of rows and the number of columns of effective pixels among the pixels are different from each other,
the pixels in the second imager are arranged in a matrix, and the number of rows and the number of columns of effective pixels among the pixels are same as a larger one out of the number of rows and the number of columns of the effective pixels in the first imager, and the display controller is configured to set one or both of the first region and a second region that is a region obtained by rotating the first region by any one of 90° and by −90° with respect to the second medical captured-image based on a predetermined selecting operation, display, when only the first region is set with respect to the second medical captured-image, the image that corresponds to the first region set with respect to the second medical captured-image on the display screen of the second display, or on the display screens of the first display and the display screen of the second display, display, when only the second region is set with respect to the second medical captured-image, an image that corresponds to the second region set with respect to the second medical captured-image on the display screen of the second display, and display, when the first region and the second region are set with respect to the second medical captured-image, the image that corresponds to the first region set with respect to the second medical captured-image on the display screen of the first display, and the image that corresponds to the second region set with respect to the second medical captured-image on the display screen of the second display.

(6)

The medical observation apparatus described in (5), wherein an orientation of the display screen of the second display is perpendicular to the display screen of the first display.

(7)

The medical observation apparatus described in any one of (1) to (3), wherein the pixels in the first imager are arranged in a matrix, and the number of rows and the number of columns of effective pixels among the pixels are different from each other, and the pixels in the second imager are arranged in a matrix, and each of the number of rows and the number of columns of effective pixels among the pixels is equal to or larger than a diameter of a circumcircle of a rectangle in which the number of rows and the number of columns of the effective pixels in the first imager constitute respective sides.

(8)

The medical observation apparatus described in (2), wherein the pixels in the first imager are arranged in a matrix, and the number of rows and the number of columns of effective pixels among the pixels are different from each other, and the pixels in the second imager are arranged in a matrix, and each of the number of rows and the number of columns of effective pixels among the pixels is equal to or larger than a diameter of a circumcircle of a rectangle in which the number of rows and the number of columns of the effective pixels in the first imager constitute respective sides, and the display controller is configured to set one or both of the first region and a third region that is a region obtained by rotating the first region with respect to the second medical captured-image based on a predetermined selecting operation, display, when only the first region is set with respect to the second medical captured-image, the image that corresponds to the first region set with respect to the second medical captured-image on the display screen of the second display, or on the display screens of the first display and the display screen of the second display, display, when only the third region is set with respect to the second medical captured-image, an image that corresponds to the third region set with respect to the second medical captured-image on the display screen of the second display, and display, when the first region and the third region are set with respect to the second medical captured-image, the image that corresponds to the first region set with respect to the second medical captured-image on the display screen of the first display, and the image that corresponds to the third region set with respect to the second medical captured-image on the display screen of the second display.

(9)

The medical observation apparatus described in (2), wherein the pixels in the first imager are arranged in a matrix, and the number of rows and the number of columns of effective pixels among the pixels are different from each other, and the pixels in the second imager are arranged in a matrix, and each of the number of rows and the number of columns of effective pixels among the pixels is equal to or larger than a diameter of a circumcircle of a rectangle in which the number of rows and the number of columns of the effective pixels in the first imager constitute respective sides, and the display controller is configured to set one or both of the first region and a fourth region that is a region obtained by rotating the first region based on a result of detection of a relative position between the camera and a predetermined observer, display, when only the first region is set with respect to the second medical captured-image, the image that corresponds to the first region set with respect to the second medical captured-image on the display screen of the second display, or on the display screens of the first display and the display screen of the second display, display, when only the fourth region is set with respect to the second medical captured-image, an image that corresponds to the fourth region set with respect to the second medical captured-image on the display screen of the second display, and display, when the first region and the fourth region are set with respect to the second medical captured-image, the image that corresponds to the first region set with respect to the second medical captured-image on the display screen of the first display, and the image that corresponds to the fourth region set with respect to the second medical captured-image on the display screen of the second display.

(10)

The medical observation apparatus described in (9), wherein the display controller is configured to set a region corresponding to the relative position with respect to the second medical captured-image each time the relative position changes.

(11)

The medical observation apparatus described in (9), wherein the display controller is configured to set a region corresponding to the relative position with respect to the second medical captured-image when a change of the relative position becomes equal to or larger than a predetermined threshold, or when the change of the relative position becomes larger than the threshold.

(12)

The medical observation apparatus described in any one of (9) to (11), wherein the display controller is configured to start setting of a region corresponding to the relative position with respect to the second medical captured-image when one or both of a position and an orientation of the camera change, and the display controller is configured not to change the region corresponding to the relative position that has been set when both of the position and the orientation of the camera have not been changing for a predetermined period since the setting of the region corresponding to the relative position is started.

(13)

The medical observation apparatus described in any one of (9) to (11), wherein the first imager and the second imager are supported by an arm constituted of multiple links connected with each other by a joint, and the display controller is configured to perform setting of a region corresponding to the relative position with respect to the second medical captured-image when an operation mode of the arm is in a first mode in which a position and an orientation of the camera are not fixed, and the display controller is configured not to change a region corresponding to the relative position that has been set, when the operation mode of the arm is a second mode in which the position and the orientation of the camera are fixed.

(14)

The medical observation apparatus described in any one of (1) to (13), wherein the total number of pixels in the first imager and the total number of pixels in the second imager are equal to each other.

(15)

The medical observation apparatus described in any one of (1) to (13), the total number of pixels in the first imager and the total number of pixels in the second imager are different from each other.

(16)

A medical observation system including
a first display;
a second display; and
a medical observation apparatus configured to display a medical captured image in which an observation target is imaged on display screens of the first display and the second display, wherein
the medical observation apparatus includes
a camera that includes
a first imager including multiple pixels, and configured to image a first medical captured-image in which an observation target is imaged, and
a second imager having multiple pixels, and configured to image a second medical captured-image in which the observation target is imaged, the second imager including more effective pixels than the first imager; and
a display controller configured to cause the first and the second display to display the first medical captured-image and an image that corresponds to a region set with respect to the second medical captured-image on a display screen of the respective one of the first and the second displays corresponding thereto.

According to the present disclosure, the convenience of a user that views a display screen on which a medical captured image is displayed can be improved.

The above effect is not necessarily limited. Along with the above effect, or in addition to the above effect, any effect described in the present application, or other effects recognizable from the present application may be produced.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical observation apparatus comprising:
a camera including
a first imager including a plurality of pixels and configured to image a first medical image in which an observation target is imaged, and
a second imager including a plurality of pixels, and configured to image a second medical image in which the observation target is imaged, the second imager including more effective pixels than the first imager; and
circuitry configured to cause displays to display the first medical image and an image that corresponds to a region set to the second medical image on a display screen of respective one of the displays corresponding thereto, wherein
one of the first medical image and the second medical image is a medical image for a right eye, and
another one of the first medical image and the second medical image is a medical image for a left eye, wherein
the pixels in the first imager are arranged in a matrix, and number of rows and number of columns of effective pixels among the pixels are different from each other, and
the pixels in the second imager are arranged in a matrix, and a number of rows and number of columns of effective pixels among the pixels are equal to or greater than a larger one out of the number of rows and the number of columns of the effective pixels in the first imager.

2. The medical observation apparatus according to claim 1, wherein the circuitry is configured to:
set one of or both of a first region having a same imaging range for the observation target as the first medical image, and a region that is obtained by rotating the first region with respect to the second medical image;
display the first medical image on a first display, or display the first medical image and an image that corresponds to the first region set to the second medical image on the first display as a stereoscopic image, and
display any one of the image that corresponds to the first region set to the second medical image, and an image that corresponds to the region obtained by rotating the first region set to the second medical image on a display screen of a second display that is different from the first display.

3. The medical observation apparatus according to claim 2, wherein the circuitry is configured to:
display the first medical image and the image that corresponds to the first region set to the second medical image on the first display, and
display the image that corresponds to the region obtained by rotating the first region set to the second medical image on the second display, and
the image displayed on the second display is an image obtained by rotating the image corresponding to the region that is obtained by rotating the first region set to the second medical image so as to be suitable for the second display.

4. The medical observation apparatus according to claim 2, wherein
the circuitry is configured to
set one or both of the first region and a second region that is a region obtained by rotating the first region by any one of 90° and by −90° with respect to the second medical image based on a predetermined selecting operation,
display, in a case where only the first region is set to the second medical image, the image that corresponds to the first region set to the second medical image on the display screen of the second display, or on the display screens of the first display and the display screen of the second display,
display, in a case where only the second region is set to the second medical image, an image that corresponds to the second region set to the second medical image on the display screen of the second display, and
display, in a case where the first region and the second region are set to the second medical image, the image that corresponds to the first region set to the second medical image on the display screen of the first display, and the image that corresponds to the second region set to the second medical image on the display screen of the second display.

5. The medical observation apparatus according to claim 4, wherein an orientation of the display screen of the second display is perpendicular to the display screen of the first display.

6. The medical observation apparatus according to claim 2, wherein
each of number of rows and number of columns of effective pixels among the pixels in the second imager is equal to or larger than a diameter of a circumcircle of a rectangle in which the number of rows and the number of columns of the effective pixels in the first imager constitute respective sides.

7. The medical observation apparatus according to claim 6, wherein
the circuitry is configured to
set one or both of the first region and a fourth region that is a region obtained by rotating the first region based on a result of detection of a relative position between the camera and a predetermined observer,
displays, in a case where only the first region is set to the second medical image, the image that corresponds to the first region set to the second medical image on the display screen of the second display, or on the display screens of the first display and the display screen of the second display,
display, in a case where only the fourth region is set to the second medical image, an image that corresponds to the fourth region set to the second medical image on the display screen of the second display, and
display, in a case where the first region and the fourth region are set to the second medical image, the image that corresponds to the first region set to the second medical image on the display screen of the first display, and the image that corresponds to the fourth region set to the second medical image on the display screen of the second display.

8. The medical observation apparatus according to claim 7, wherein the circuitry is configured to set a region corresponding to the relative position with respect to the second medical image each time the relative position changes.

9. The medical observation apparatus according to claim 7, wherein the circuitry is configured to set a region corresponding to the relative position with respect to the second medical image in a case where a change of the relative position becomes equal to or larger than a predetermined threshold, or in a case where the change of the relative position becomes larger than the threshold.

10. The medical observation apparatus according to claim 7, wherein
the circuitry is configured to start setting of a region corresponding to the relative position with respect to the second medical image in a case where one or both of a position and an orientation of the camera change, and
the circuitry is configured not to change the region corresponding to the relative position that has been set in a case where both of the position and the orientation of the camera have not been changing for a predetermined period since the setting of the region corresponding to the relative position is started.

11. The medical observation apparatus according to claim 7, wherein
the first imager and the second imager are supported by an arm including a plurality of links connected with each other by a joint, and
the circuitry is configured to perform setting of a region corresponding to the relative position with respect to the second medical image in a case where an operation mode of the arm is in a first mode in which a position and an orientation of the camera are not fixed, and
the circuitry is configured not to change a region corresponding to the relative position that has been set, in a case where the operation mode of the arm is a second mode in which the position and the orientation of the camera are fixed.

12. The medical observation apparatus according to claim 1, wherein
each of number of rows and number of columns of effective pixels among the pixels in the second imager is equal to or larger than a diameter of a circumcircle of a rectangle in which the number of rows and the number of columns of the effective pixels in the first imager constitute respective sides.

13. A medical observation system comprising:
a first display;
a second display;
a medical observation apparatus configured to display a medical image in which an observation target is imaged on display screens of the first display and the second display, wherein
the medical observation apparatus includes:
a camera that includes
a first imager including a plurality of pixels and configured to image a first medical image in which the observation target is imaged, and
a second imager including a plurality of pixels and configured to image a second medical image in which the observation target is imaged, the second imager including more effective pixels than the first imager; and
circuitry configured to cause the first and the second displays to display the first medical image and an image that corresponds to a region set to the second medical image on a display screen of respective one of the first and the second displays corresponding thereto, wherein
the pixels in the first imager are arranged in a matrix, and number of rows and number of columns of effective pixels among the pixels are different from each other, and the pixels in the second imager are arranged in a matrix, and a number of rows and a number of columns of effective pixels among the pixels are equal to or greater than a larger one out of the number of rows and the number of columns of the effective pixels in the first imager.

14. The medical observation system according to claim 13, wherein
each of number of rows and number of columns of effective pixels in the second imager among the pixels is equal to or larger than a diameter of a circumcircle of a rectangle in which the number of rows and the number of columns of the effective pixels in the first imager constitute respective sides.

15. The medical observation system according to claim 14, wherein the circuitry is configured to:
set one of or both of a first region having a same imaging range for the observation target as the first medical image, and a region that is obtained by rotating the first region with respect to the second medical image;
display the first medical image on a first display, or display the first medical image and an image that corresponds to the first region set to the second medical image on the first display as a stereoscopic image;
display any one of the image that corresponds to the first region set to the second medical image, and an image that corresponds to the region obtained by rotating the first region set to the second medical image on a display screen of a second display that is different from the first display;
set one or both of the first region and a second region that is a region obtained by rotating the first region with respect to the second medical image based on a predetermined selecting operation or by rotating the first region based on a result of detection of a relative position between the camera and a predetermined observer;
display, in a case where only the first region is set to the second medical image, the image that corresponds to the first region set to the second medical image on the display screen of the second display, or on the display screens of the first display and the display screen of the second display;
display, in a case where only the second region is set to the second medical image, an image that corresponds to the second region set to the second medical image on the display screen of the second display; and
display, in a case where the first region and the second region are set to the second medical image, the image that corresponds to the first region set to the second medical image on the display screen of the first display, and the image that corresponds to the second region set to the second medical image on the display screen of the second display.

16. The medical observation system according to claim 13, wherein the circuitry is configured to:
set one of or both of a first region having a same imaging range for the observation target as the first medical image, and a region that is obtained by rotating the first region with respect to the second medical image;
display the first medical image on a first display, or display the first medical image and an image that corresponds to the first region set to the second medical image on the first display as a stereoscopic image;
display any one of the image that corresponds to the first region set to the second medical image, and an image that corresponds to the region obtained by rotating the first region set to the second medical image on a display screen of a second display that is different from the first display;
set one or both of the first region and a second region that is a region obtained by rotating the first region with respect to the second medical image based on a predetermined selecting operation or by rotating the first region based on a result of detection of a relative position between the camera and a predetermined observer;
display, in a case where only the first region is set to the second medical image, the image that corresponds to the first region set to the second medical image on the display screen of the second display, or on the display screens of the first display and the display screen of the second display;
display, in a case where only the second region is set to the second medical image, an image that corresponds to the second region set to the second medical image on the display screen of the second display; and
display, in a case where the first region and the second region are set to the second medical image, the image that corresponds to the first region set to the second medical image on the display screen of the first display, and the image that corresponds to the second region set to the second medical image on the display screen of the second display.

* * * * *